US012357192B2

(12) United States Patent
van der Weide et al.

(10) Patent No.: US 12,357,192 B2
(45) Date of Patent: *Jul. 15, 2025

(54) SURGICAL DEVICE GUIDANCE AND MONITORING DEVICES, SYSTEMS, AND METHODS

(71) Applicant: Elucent Medical, Inc., Eden Prairie, MN (US)

(72) Inventors: Daniel W. van der Weide, Madison, WI (US); Noah van der Weide, Madison, WI (US); Eric N. Rudie, Maple Grove, MN (US); David Miel, Minneapolis, MN (US); Lee G. Wilke, Eden Prairie, MN (US); Fred T. Lee, Jr., Eden Prairie, MN (US)

(73) Assignee: Elucent Medical, Inc., Eden Prairie, MN (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/686,760

(22) Filed: Mar. 4, 2022

(65) Prior Publication Data

US 2022/0183585 A1 Jun. 16, 2022

Related U.S. Application Data

(63) Continuation of application No. 16/199,583, filed on Nov. 26, 2018, now Pat. No. 11,298,044, which is a
(Continued)

(51) Int. Cl.
*A61B 5/06* (2006.01)
*A61B 5/00* (2006.01)
(Continued)

(52) U.S. Cl.
CPC ............ *A61B 5/062* (2013.01); *A61B 5/0068* (2013.01); *A61B 5/06* (2013.01); *A61B 5/064* (2013.01);
(Continued)

(58) Field of Classification Search
None
See application file for complete search history.

(56) References Cited

U.S. PATENT DOCUMENTS

| 3,689,885 A | 9/1972 | Kaplan et al. |
| 3,706,094 A | 12/1972 | Cole et al. |

(Continued)

FOREIGN PATENT DOCUMENTS

| CN | 101069640 | 11/2007 |
| CN | 102264292 | 11/2011 |

(Continued)

OTHER PUBLICATIONS

Li et al., Radio frequency identification technology: applications, technical challenges and strategies, Management Department Journal Article, 2006, paper 34, 28 pages.
(Continued)

*Primary Examiner* — Baisakhi Roy
(74) *Attorney, Agent, or Firm* — CASIMIR JONES, S.C.; Brian F. Bradley

(57) ABSTRACT

Provided herein are systems, devices, assemblies, and methods for localization of one or more tags in a patient.

24 Claims, 15 Drawing Sheets

Related U.S. Application Data continuation of application No. 15/674,455, filed on Aug. 10, 2017, now Pat. No. 10,154,799.

(60) Provisional application No. 62/491,887, filed on Apr. 28, 2017, provisional application No. 62/374,402, filed on Aug. 12, 2016.

(51) Int. Cl.
*A61B 34/20* (2016.01)
*G06K 7/10* (2006.01)
*A61B 6/42* (2024.01)
*A61B 18/04* (2006.01)
*A61B 18/08* (2006.01)
*A61B 90/00* (2016.01)
*H01Q 1/22* (2006.01)

(52) U.S. Cl.
CPC .............. *A61B 5/066* (2013.01); *A61B 5/743* (2013.01); *A61B 34/20* (2016.02); *G06K 7/10386* (2013.01); *A61B 5/6886* (2013.01); *A61B 6/4241* (2013.01); *A61B 18/04* (2013.01); *A61B 18/08* (2013.01); *A61B 2034/2051* (2016.02); *A61B 2090/061* (2016.02); *A61B 90/39* (2016.02); *A61B 2505/05* (2013.01); *H01Q 1/2208* (2013.01); *H01Q 1/2225* (2013.01)

(56) References Cited

U.S. PATENT DOCUMENTS

| | | | |
|---|---|---|---|
| 4,494,545 A | 1/1985 | Slocum et al. | |
| 4,561,443 A | 12/1985 | Hogrefe et al. | |
| 4,804,054 A | 2/1989 | Howson et al. | |
| 5,012,236 A | 4/1991 | Troyk et al. | |
| 5,095,309 A | 3/1992 | Troyk et al. | |
| 5,142,292 A | 8/1992 | Chang | |
| 5,198,807 A | 3/1993 | Troyk et al. | |
| 5,221,831 A | 6/1993 | Geiszler et al. | |
| 5,241,961 A | 9/1993 | Henry | |
| 5,752,513 A | 5/1998 | Acker et al. | |
| 5,867,101 A | 2/1999 | Copeland et al. | |
| 6,020,856 A | 2/2000 | Alicot | |
| 6,026,818 A | 2/2000 | Blair et al. | |
| 6,047,214 A | 4/2000 | Mueller et al. | |
| 6,053,873 A | 4/2000 | Govari et al. | |
| 6,069,564 A | 5/2000 | Hatano et al. | |
| 6,198,963 B1 | 3/2001 | Haim et al. | |
| 6,249,212 B1 | 6/2001 | Beigel et al. | |
| 6,263,247 B1 | 7/2001 | Mueller et al. | |
| 6,361,532 B1 | 3/2002 | Burek | |
| 6,363,940 B1 | 4/2002 | Krag | |
| 6,499,488 B1 | 12/2002 | Hunter et al. | |
| 6,675,810 B2 | 1/2004 | Krag | |
| 6,698,433 B2 | 3/2004 | Krag | |
| 6,765,476 B2 | 7/2004 | Steele et al. | |
| 6,784,788 B2 | 8/2004 | Beigel et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,889,833 B2 | 5/2005 | Seiler et al. | |
| 6,977,504 B2 | 12/2005 | Wright et al. | |
| 7,007,699 B2 | 3/2006 | Martinelli et al. | |
| 7,023,391 B2 | 4/2006 | Wuidart et al. | |
| 7,026,927 B2 | 4/2006 | Wright et al. | |
| 7,135,978 B2 | 11/2006 | Gisselberg et al. | |
| 7,174,201 B2 | 2/2007 | Govari et al. | |
| 7,176,798 B2 | 2/2007 | Dimmer et al. | |
| 7,289,839 B2 | 10/2007 | Dimmer et al. | |
| 7,307,530 B2 | 12/2007 | Fabian et al. | |
| 7,319,396 B2 | 1/2008 | Homanfar et al. | |
| 7,347,379 B2 | 3/2008 | Ward et al. | |
| 7,366,562 B2 | 4/2008 | Dukesherer et al. | |
| 7,407,054 B2 | 8/2008 | Seiler et al. | |
| 7,411,505 B2 | 8/2008 | Smith et al. | |
| 7,414,404 B2 | 8/2008 | Keene | |
| 7,420,468 B2 | 9/2008 | Fabian et al. | |
| 7,474,223 B2 | 1/2009 | Nycz et al. | |
| 7,518,518 B2 | 4/2009 | Homanfar et al. | |
| 7,549,960 B2 | 6/2009 | Govari | |
| 7,558,616 B2 | 7/2009 | Govari et al. | |
| 7,575,550 B1 | 8/2009 | Govari | |
| 7,590,441 B2 | 9/2009 | Govari et al. | |
| 7,632,270 B2 | 12/2009 | Livneh | |
| 7,657,301 B2 | 2/2010 | Mate et al. | |
| 7,657,302 B2 | 2/2010 | Mate et al. | |
| 7,657,303 B2 | 2/2010 | Mate et al. | |
| 7,684,849 B2 | 3/2010 | Wright et al. | |
| 7,696,876 B2 | 4/2010 | Dimmer et al. | |
| 7,715,898 B2 | 5/2010 | Anderson | |
| 7,747,307 B2 | 6/2010 | Wright et al. | |
| 7,751,865 B2 | 7/2010 | Jascob et al. | |
| 7,778,687 B2 | 8/2010 | Dimmer et al. | |
| 7,814,916 B2 | 10/2010 | Revie et al. | |
| 7,817,040 B2 | 10/2010 | Homanfar et al. | |
| 7,818,044 B2 | 10/2010 | Dukesherer et al. | |
| 7,840,253 B2 | 11/2010 | Tremblay et al. | |
| 7,848,553 B2 | 12/2010 | Hertel et al. | |
| 7,871,423 B2 | 1/2011 | Livneh | |
| 7,899,513 B2 | 3/2011 | Phillips et al. | |
| 7,912,529 B2 | 3/2011 | Herron et al. | |
| 7,926,491 B2 | 4/2011 | Wright et al. | |
| 7,971,341 B2 | 7/2011 | Dukesherer et al. | |
| 7,993,335 B2 | 8/2011 | Rioux et al. | |
| 8,011,508 B2 | 9/2011 | Seiler et al. | |
| 8,012,154 B2 | 9/2011 | Livneh | |
| 8,057,407 B2 | 11/2011 | Martinelli et al. | |
| 8,057,468 B2 | 11/2011 | Konesky | |
| 8,100,897 B2 | 1/2012 | Zoran | |
| 8,113,210 B2 | 2/2012 | Petcavich et al. | |
| 8,114,181 B2 | 2/2012 | Gogolin | |
| 8,196,589 B2 | 6/2012 | Gisselberg et al. | |
| 8,226,640 B2 | 7/2012 | Zoran | |
| 8,239,001 B2 | 8/2012 | Verard et al. | |
| 8,271,069 B2 | 9/2012 | Jascob et al. | |
| 8,354,837 B2 | 1/2013 | Anderson | |
| 8,359,730 B2 | 1/2013 | Burg et al. | |
| 8,377,388 B2 | 2/2013 | Konesky | |
| 8,399,837 B2 | 3/2013 | Robbins et al. | |
| 8,409,190 B2 | 4/2013 | Konesky et al. | |
| 8,467,852 B2 | 6/2013 | Csavoy et al. | |
| 8,549,732 B2 | 10/2013 | Burg et al. | |
| 8,628,524 B2 | 1/2014 | Shilev | |
| 8,644,907 B2 | 2/2014 | Hartmann et al. | |
| 8,647,342 B2 | 2/2014 | Livneh | |
| 8,696,663 B2 | 4/2014 | Pardoll et al. | |
| 8,728,076 B2 | 5/2014 | Livneh | |
| 8,795,265 B2 | 8/2014 | Konesky et al. | |
| 8,795,272 B2 | 8/2014 | Rioux et al. | |
| 8,802,022 B2 | 8/2014 | Konesky | |
| 8,830,037 B2 | 9/2014 | Burke et al. | |
| 8,857,043 B2 | 10/2014 | Dimmer et al. | |
| 8,892,185 B2 | 11/2014 | Chi Sing et al. | |
| 8,939,153 B1 | 1/2015 | Reicher et al. | |
| 8,948,845 B2 | 2/2015 | Glossop et al. | |
| 8,968,171 B2 | 3/2015 | McKenna et al. | |
| 8,973,584 B2 | 3/2015 | Brander et al. | |
| 8,979,834 B2 | 3/2015 | Zoran et al. | |
| 8,998,899 B2 | 4/2015 | Shilev et al. | |
| 9,002,434 B2 | 4/2015 | Uchiyama et al. | |
| 9,060,765 B2 | 6/2015 | Rencher et al. | |
| 9,095,333 B2 | 8/2015 | Konesky et al. | |
| 9,144,453 B2 | 9/2015 | Rencher et al. | |
| 9,234,877 B2 | 1/2016 | Hattersley et al. | |
| 9,239,314 B2 | 1/2016 | Hattersley et al. | |
| 9,730,764 B2 | 8/2017 | Van Der Weide et al. | |
| 9,987,097 B2* | 6/2018 | van der Weide | G06K 7/12 |
| 10,154,799 B2* | 12/2018 | van der Weide | A61B 5/062 |
| 10,245,118 B2 | 4/2019 | Van Der Weide et al. | |
| 10,245,119 B2* | 4/2019 | van der Weide | G06K 7/12 |
| 10,278,779 B1 | 5/2019 | Rudie et al. | |
| 11,298,044 B2* | 4/2022 | van der Weide | A61B 5/06 |

(56) References Cited

U.S. PATENT DOCUMENTS

| | | |
|---|---|---|
| 2003/0018246 A1 | 1/2003 | Govari et al. |
| 2003/0117269 A1 | 6/2003 | Dimmer |
| 2003/0120150 A1 | 6/2003 | Govari |
| 2003/0153850 A1 | 8/2003 | Davis et al. |
| 2004/0093187 A1 | 5/2004 | Dames et al. |
| 2004/0123871 A1 | 7/2004 | Wright et al. |
| 2004/0169505 A1 | 9/2004 | Alun et al. |
| 2004/0199067 A1 | 10/2004 | Bock et al. |
| 2005/0020909 A1 | 1/2005 | Moctezuma De et al. |
| 2006/0093089 A1 | 5/2006 | Vertatschitsch et al. |
| 2006/0187044 A1* | 8/2006 | Fabian ............... A61B 5/06 340/572.1 |
| 2007/0232882 A1 | 10/2007 | Glossop et al. |
| 2008/0125630 A1 | 5/2008 | Caylor |
| 2008/0132860 A1 | 6/2008 | Smith et al. |
| 2008/0190438 A1* | 8/2008 | Harlev ............ A61B 5/0538 128/898 |
| 2008/0194912 A1 | 8/2008 | Trovato et al. |
| 2008/0208041 A1* | 8/2008 | Gilboa ................ G06T 7/73 600/426 |
| 2008/0213382 A1 | 9/2008 | Ivkov et al. |
| 2008/0281190 A1 | 11/2008 | Petcavich et al. |
| 2009/0253976 A1* | 10/2009 | Harlev ............ A61B 5/343 606/41 |
| 2009/0281419 A1 | 11/2009 | Troesken et al. |
| 2010/0004523 A1 | 1/2010 | August et al. |
| 2010/0106154 A1* | 4/2010 | Harlev ............ A61B 34/20 600/407 |
| 2010/0171492 A1* | 7/2010 | Klocke ............ A61B 34/20 324/228 |
| 2010/0274145 A1 | 10/2010 | Tupin et al. |
| 2010/0275934 A1 | 11/2010 | Keren |
| 2010/0305430 A1 | 12/2010 | Troesken et al. |
| 2011/0046481 A1 | 2/2011 | Mate et al. |
| 2011/0152677 A1 | 6/2011 | Faul |
| 2011/0201923 A1 | 8/2011 | Shen |
| 2011/0278948 A1 | 11/2011 | Forsell |
| 2012/0025985 A1* | 2/2012 | Bolander ............ G16H 10/40 340/572.1 |
| 2012/0082342 A1 | 4/2012 | Kim et al. |
| 2013/0052953 A1 | 2/2013 | Rofougaran |
| 2013/0345561 A1 | 12/2013 | Quigley |
| 2014/0018663 A1 | 1/2014 | Harmer et al. |
| 2014/0062717 A1 | 3/2014 | Mudumbai et al. |
| 2014/0066754 A1 | 3/2014 | Chi Sing et al. |
| 2014/0148692 A1 | 5/2014 | Hartmann et al. |
| 2014/0148808 A1 | 5/2014 | Inkpen et al. |
| 2014/0171792 A1 | 6/2014 | Dalal et al. |
| 2014/0309522 A1 | 10/2014 | Fullerton et al. |
| 2015/0100109 A1* | 4/2015 | Feldman ............ A61N 1/3787 607/60 |
| 2015/0129664 A1 | 5/2015 | Brar |
| 2015/0141811 A1 | 5/2015 | Ritchey et al. |
| 2015/0196369 A1 | 7/2015 | Glossop et al. |
| 2015/0264891 A1 | 9/2015 | Brander et al. |
| 2016/0022216 A1 | 1/2016 | Goldshtein et al. |
| 2016/0051164 A1 | 2/2016 | Derichs et al. |
| 2016/0192960 A1 | 7/2016 | Bueno et al. |
| 2016/0374644 A1* | 12/2016 | Mauldin, Jr. ......... A61B 8/085 600/424 |
| 2017/0095313 A1 | 4/2017 | Van Der Weide et al. |
| 2017/0095315 A1 | 4/2017 | Van Der Weide et al. |
| 2017/0238996 A1* | 8/2017 | Frame ............... A61B 34/20 |
| 2017/0312046 A1 | 11/2017 | Van Der Weide et al. |
| 2019/0209263 A1 | 7/2019 | Van Der Weide et al. |
| 2019/0239980 A1 | 8/2019 | Van Der Weide et al. |
| 2019/0365478 A1 | 12/2019 | Rudie et al. |
| 2019/0388178 A1 | 12/2019 | Rudie et al. |

FOREIGN PATENT DOCUMENTS

| | | |
|---|---|---|
| DE | 10112303 | 10/2002 |
| DE | 102011006537 | 10/2012 |
| EP | 1232730 | 8/2002 |
| JP | 2005-121573 | 5/2005 |
| JP | 2012-524627 | 10/2012 |
| WO | WO 1993/005707 | 4/1993 |
| WO | WO 2007/064013 | 6/2007 |
| WO | WO 2010/058150 | 5/2010 |
| WO | WO 2010/124117 | 10/2010 |
| WO | WO 2012/109760 | 8/2012 |
| WO | WO 2015/23665 | 2/2015 |
| WO | WO 2015039039 | 3/2015 |
| WO | WO 2015/063280 | 5/2015 |
| WO | WO 2015112863 | 1/2016 |
| WO | WO 2017059228 | 4/2017 |
| WO | WO 2018/031826 | 2/2018 |
| WO | WO 2019/236600 | 12/2019 |

OTHER PUBLICATIONS

Luini et al., Comparison of Radioguided excision with wire localization of occult breast lesions, Br. J. Surg, 1999, 86:522-525.

Mickle et al., Intellectual Property and Ubiquitos RFID, Recent Patents on Electrical Engineering, 2008, 1:59-67.

Radio Frequency Identification: Opportunites and Challenges in Immpementation, Department of Commerce, 2005, Washington D.C., 38 pages.

Shah et al, Expanding the use of real-time electromagnetic tracking in radiation oncology, J Appl Clin Med Phys. Nov. 15, 2011; 12(4):3590.

Shantz, A Near Field Propagation Law & A Novel Fundamental Limit to Antenna Gain Versus Size. Antennas and Propagation Society International Symposium, 2005 IEEE, Jul. 3-8, 2005, Washington D.C. 4 pages.

Soon, Radio Frequency Identification History and Development, Chapt. 1, Ubiquitous and Pervasive Computing: Concepts, Methodologies, Tools, and Applications, 2010, ed. Symonds, 17 pages.

Stockman, Communication by Means of Reflected Power, Proceedings of the I.R.E., 1948, 36(10):1196-1204.

Takahata et al., Thoracoscopic surgery support system using passive RFID marker, 34th Annual International Conference of the IEEE EMBS, San Diego, CA, Aug. 28-Sep. 1, 2012, pp. 183-186.

Van Lieshout et al., RFID Technologies: Emerging Issues, Challenges and Policy Options, JRC Scientific and Technical Reports, 2007, 278 pages.

Want, RFID: A Key to Automating Everything, Scientific American, Inc., Jan. 2004, pp. 56-63.

International Search Report and Written Opinion, mailed May 5, 2015, for PCT/US2015/012687, 11 pages.

International Search Report and Written Opinion for PCT/US2016/054738, mailed Jan. 31, 2017, 9 pages.

European Supplemental Search Report for EP15740262.9, mailed Sep. 18, 2017, 14 pages.

International Search Report and Written Opinion for PCT/US2017/046379, mailed Dec. 5, 2017, 15 pages.

European Supplemental Search Report for EP16852699.4, mailed May 10, 2019, 10 pages.

International Search Report and Written Opinion for PCT/US2019/035424, mailed Oct. 24, 2019, 13 pages.

European Search Report for EP17840310.1, mailed Mar. 30, 2020, 11 pages.

Extended European Search Report, EP Patent Application No. 23211243.3, dated Feb. 19, 2024, 4 pages.

\* cited by examiner

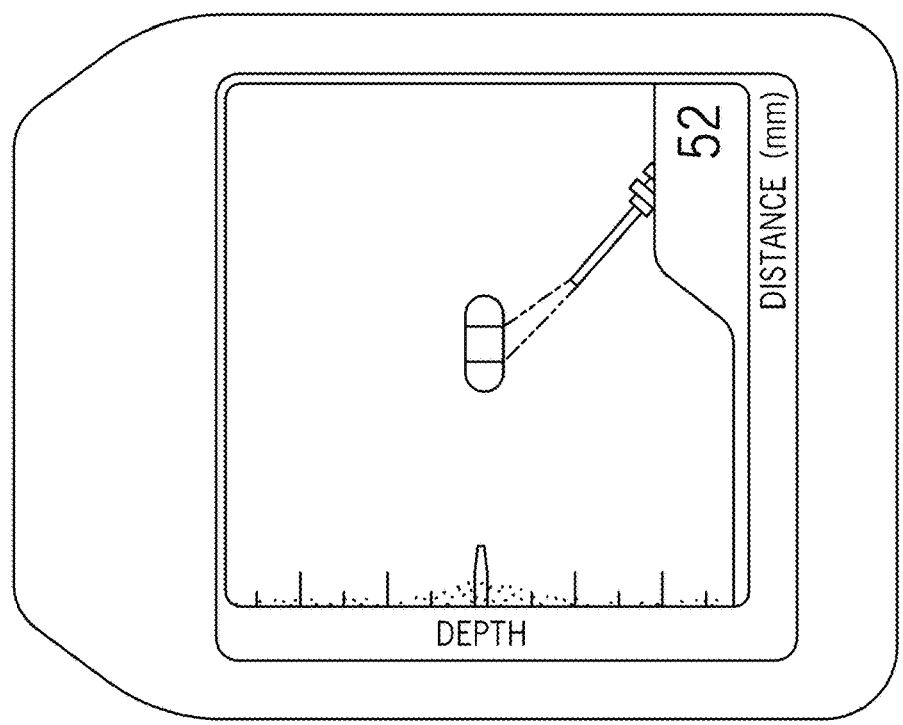
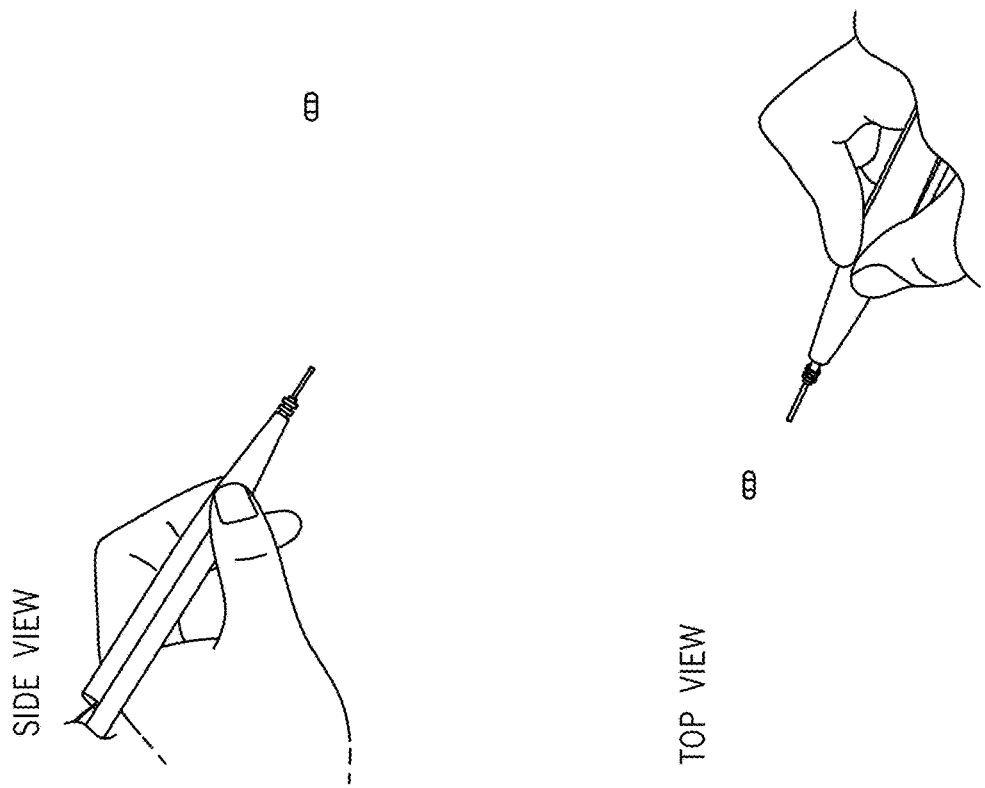
FIG. 11

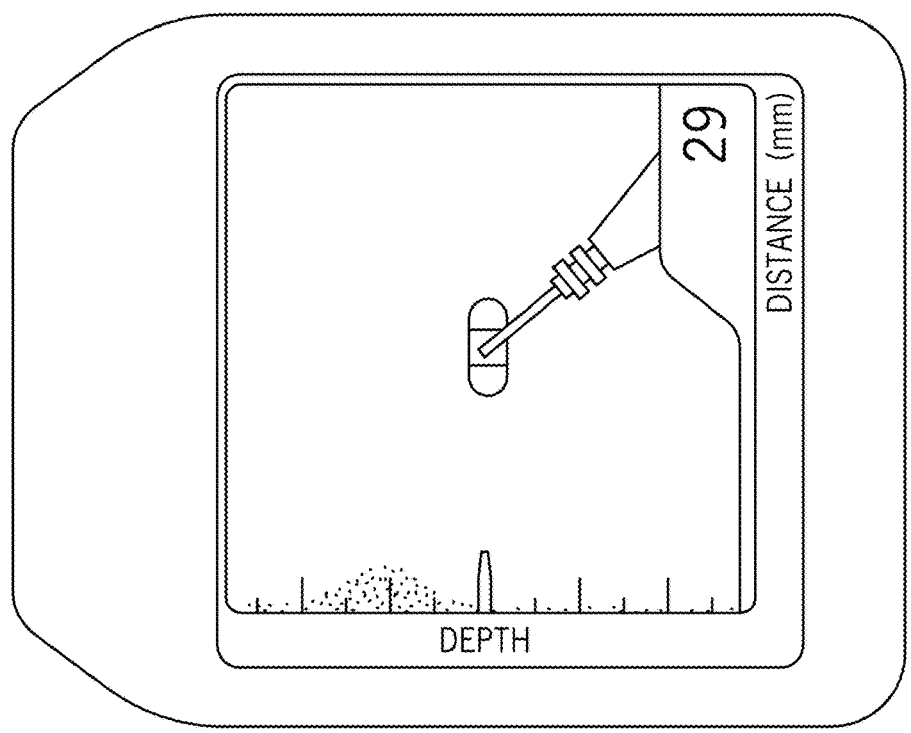
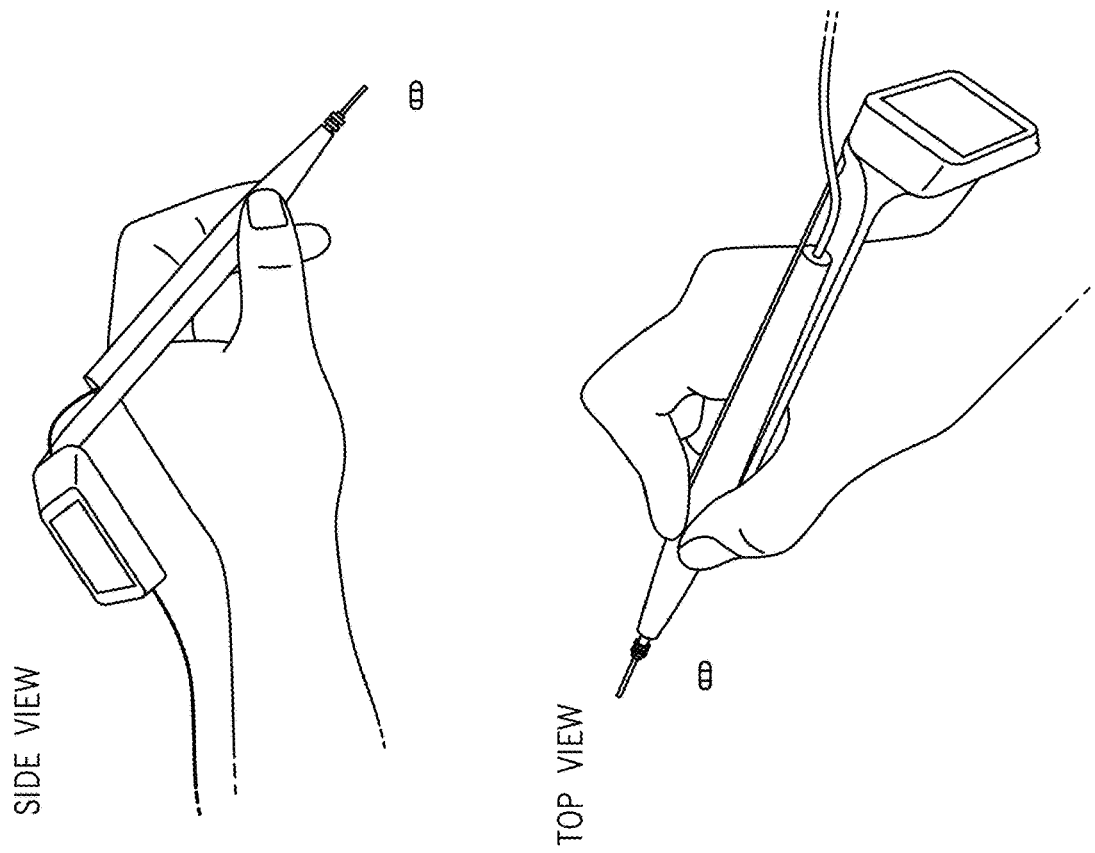
FIG. 12

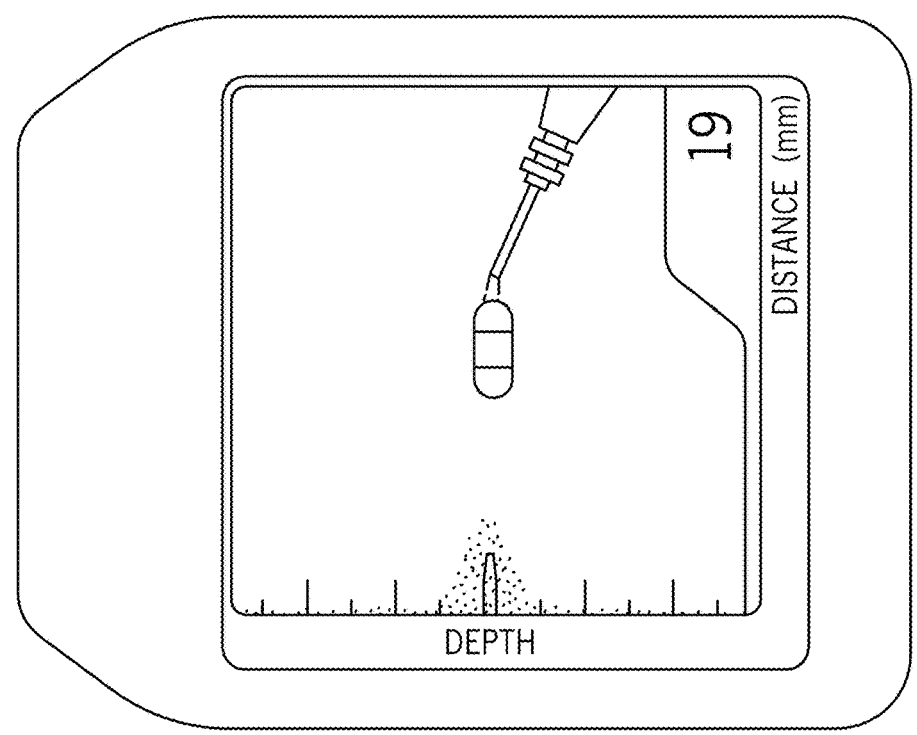
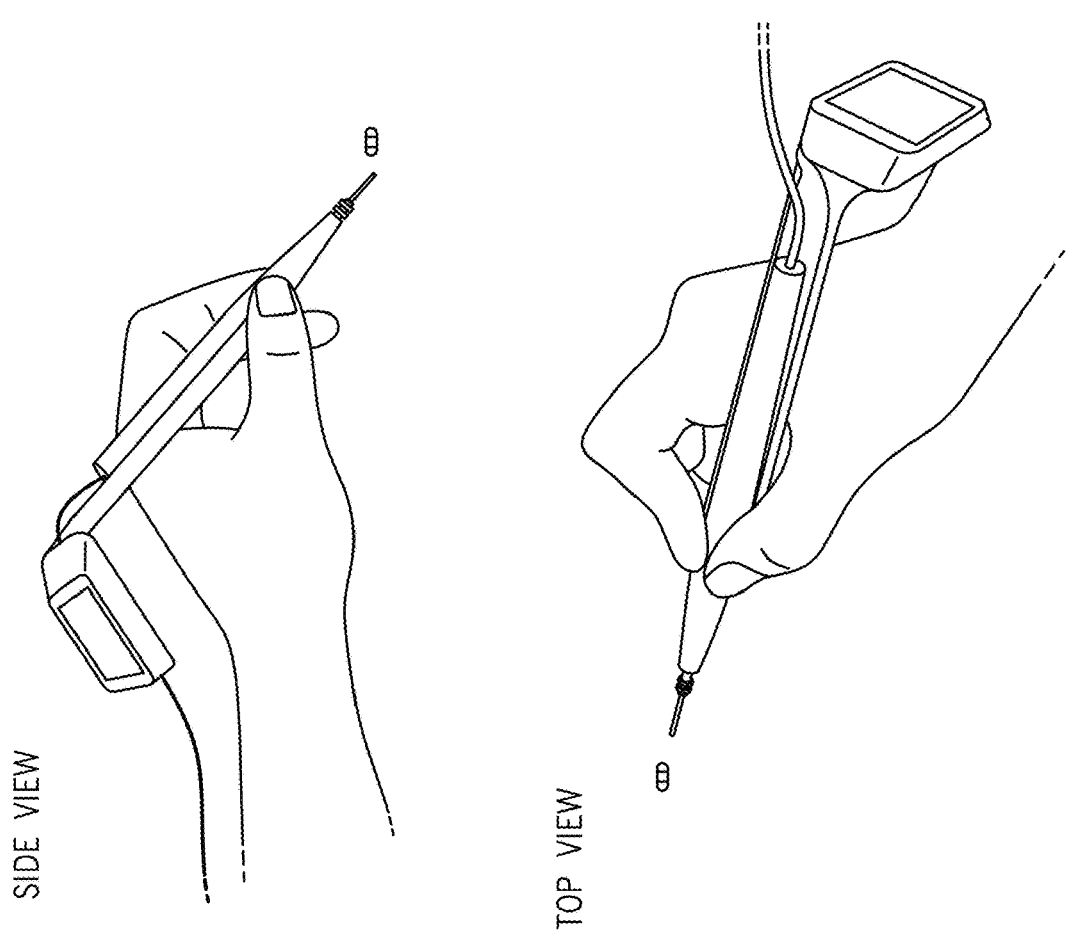
FIG. 13

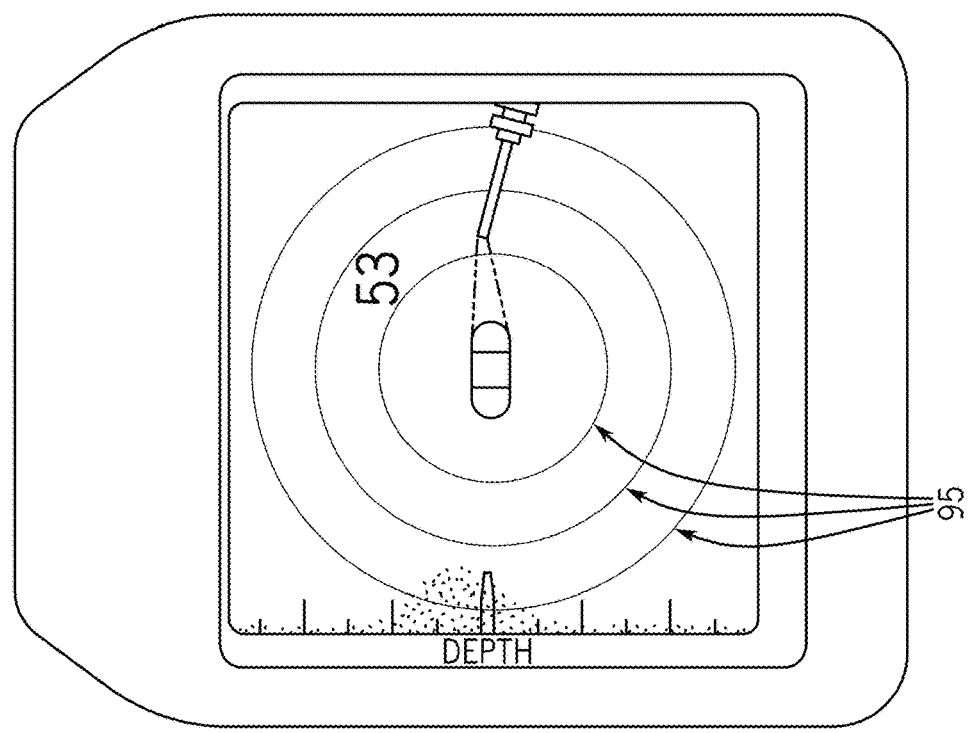
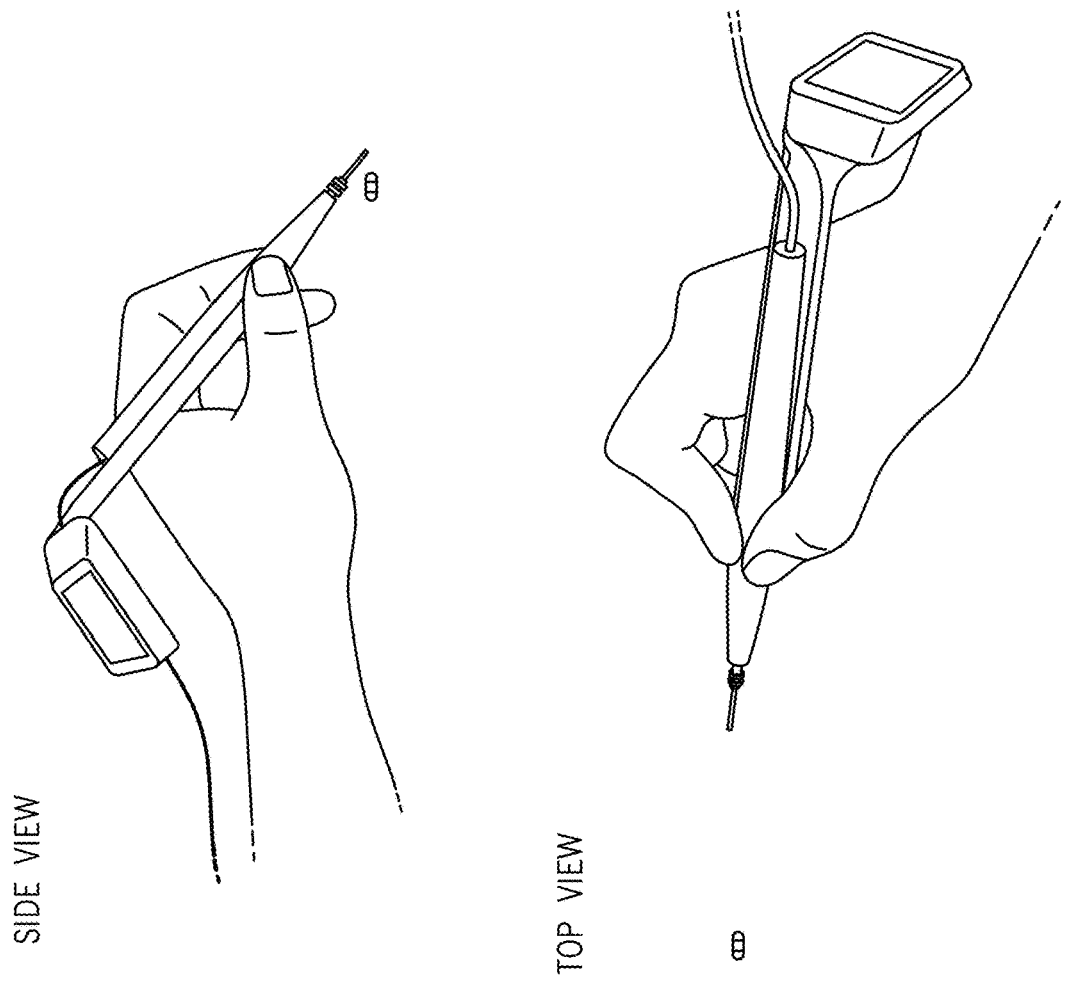
FIG. 14

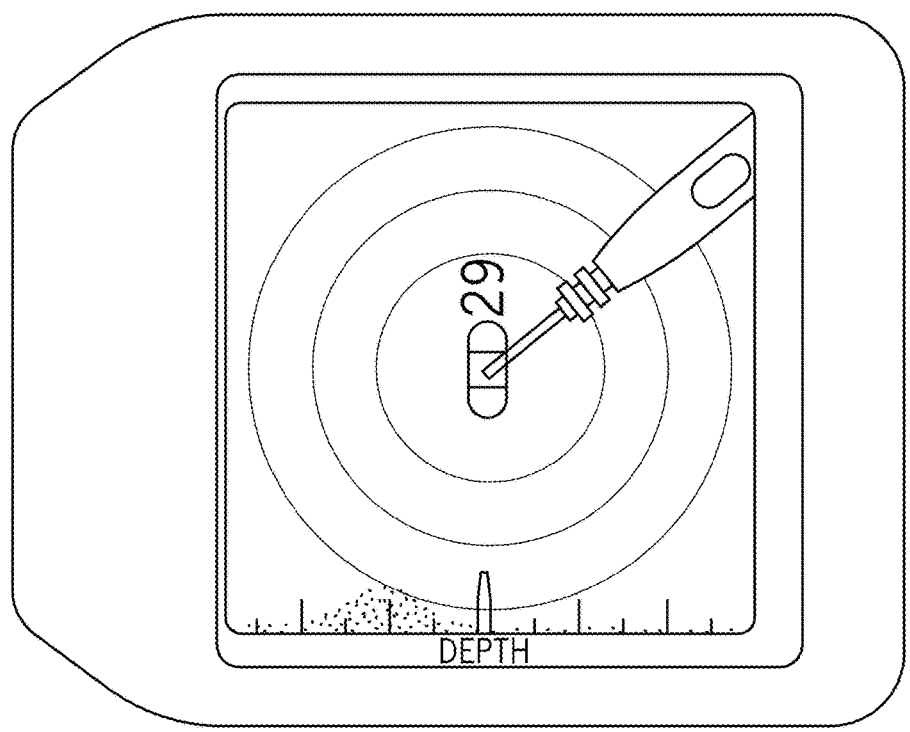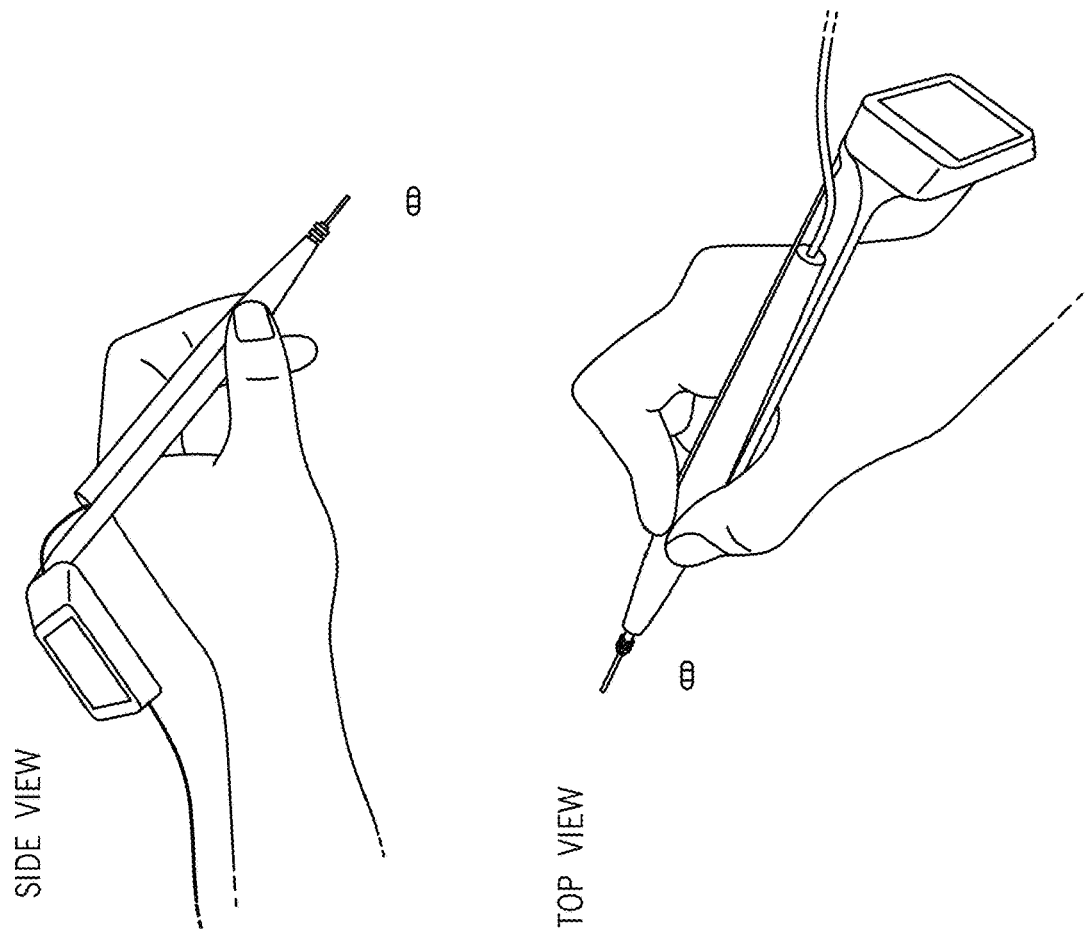
FIG. 15

SURGICAL DEVICE GUIDANCE AND MONITORING DEVICES, SYSTEMS, AND METHODS

CROSS-REFERENCE FOR RELATED APPLICATIONS

The present invention is a continuation of U.S. patent application Ser. No. 16/199,583, filed Nov. 26, 2018, which is a continuation of U.S. patent application Ser. No. 15/674,455, filed Aug. 10, 2017, now U.S. Pat. No. 10,154,799, which claims the priority benefit of U.S. Provisional Patent Application Ser. No. 62/374,402, filed Aug. 12, 2016 and U.S. Provisional Patent Application Ser. No. 62/491,887, filed Apr. 28, 2017, each of which are incorporated by reference in their entirety.

FIELD

Provided herein are systems, devices, assemblies, and methods for localization of one or more tags in a patient.

BACKGROUND

A common and serious challenge for many medical procedures is the accurate localization of treatment areas. For example, the location of lesions, such as tumors that are to undergo treatment, including surgical resection, continues to present a challenge to the medical community. Existing systems are expensive, complex, time-consuming, and often unpleasant for the patient. Such issues are illustrated by the surgical treatment of breast lesions.

A common technique used in breast tumor surgery is wire localization of the lesions. Precise preoperative localization of some breast lesions is necessary before removal of the lesion. Wire localization is used to mark the location of a breast abnormality. The procedure ensures greater accuracy for a breast biopsy or lumpectomy. The surgeon typically uses the wire as a guide to the tissue that needs to be removed. Wire localization is typically conducted in the radiology department of the hospital or surgical center. Mammograms (or in some cases, ultrasound images) are taken to show the location of the breast abnormality. Patients are awake during the placement of the wire, but the breast tissue is numbed to reduce or avoid pain from the needle or the wire. It is possible to feel pressure or pulling sensations during the wire placement. Once images have been taken, and the tissue has been numbed, the radiologist will use a needle to target the breast abnormality. The tip of this needle rests in the location that the surgeon needs to find in order to remove the right tissue. A slender wire is threaded down through the needle and out of its tip, to lodge at the target tissue. The needle is removed, leaving the wire in place. With the wire in place, the patient has another mammogram, to check that the tip of the wire is properly positioned. If the wire is not in the correct place, the radiologist will reposition and re-check it, to ensure accurate placement. When the wire is finally positioned, it will be secured in place with tape or a bandage. The wire localization procedure can take about an hour, and is usually scheduled hours before biopsy or lumpectomy. Thus, the patient must often wait hours for surgery with the wire present in their body and protruding from their skin. The wire is removed, along with some breast tissue, during surgery. This process takes many hours, involves multiple imaging steps, and is inconvenient and unpleasant for the patient—as well as being expensive.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is placed in or around the nodule in an attempt to improve localization prior to removal. This procedure usually takes place in the computerized tomography (CT) suite prior to the removal of the nodule. The patient is then transported to the surgical unit and the surgeon cuts down on the wire, uses a radionuclide detector, or uses visual landmarks to localize and remove the nodule.

In other types of surgeries and medical procedures, physicians may have trouble locating a target prior to removal or manipulation. Examples of this include the removal of masses, fluid collections, foreign bodies or diseased tissues. Other times, placements of catheters or other percutaneous procedures are performed either without direct visualization or with the lack of a specific guidance modality. Performing procedures without precise guidance can increase the amount of damage to normal tissues and decrease the patient's functional status.

Percutaneous biopsy is a well-accepted, safe procedure performed in virtually every hospital. Biopsy often entails placement of a co-axial guide needle through which the biopsy device is placed into the target. Many of the lesions that are removed, punctured or manipulated as described above have previously undergone successful percutaneous biopsy. The placement of the guide needle for biopsy is an opportunity to place a fiduciary or other localizing system without causing additional tissue trauma than the patient would otherwise undergo.

Many other medical devices and procedures could benefit from improved tissue localization. These include any procedure or test that is degraded by any bodily motion such as cardiac motion, respiratory motion, motion produced by the musculoskeletal system, or gastrointestinal/genitourinary motion. Examples of these include external beam radiation therapy, placement of brachytherapy seeds, imaging tests including but not limited to CT, MRI, fluoroscopy, ultrasound, and nuclear medicine, biopsies performed in any fashion, endoscopy, laparoscopic and thoracoscopic surgery and open surgical procedures.

Improved systems and methods are needed for tissue localization for medical procedure.

SUMMARY

Provided herein are systems, devices, assemblies, and methods for localization of one or more tags in a patient. The systems, devices, assemblies, and method find use in non-medical settings as well.

In certain embodiments, provided herein are systems and kits and devices comprising: a) an attachment component comprising at least one location emitter, wherein the attachment component is configured to be attached to a hand-held medical device with a device tip; and b) a display component: i) attached to, ii) integral with, or iii) configured to be attached to, the attachment component, wherein the display component comprises a display screen, and wherein the display screen displays: i) a tag indicator (e.g., tag schematic) which corresponds to the physical location of a tag (e.g. a tag with an antenna, such as an RFID tag) or other fiducial.

In particular embodiments, provided herein are systems and kits and devices comprising: a) an attachment component comprising at least one location emitter, wherein the attachment component is configured to be attached to a hand-held medical device with a device tip; and b) a display component: i) attached to, ii) integral with, or iii) configured to be attached to, the attachment component, wherein the display component comprises a display screen, and wherein the display screen displays information relevant to the use of the hand-held medical device in performing a surgical procedure. In certain embodiments, the display screen is in-line with a user's (e.g., surgeon's) line of sight.

In some embodiments, provided herein are systems and kits and devices comprising: a) an attachment component comprising at least one location emitter, wherein the attachment component is configured to be attached to a hand-held medical device with a device tip; and b) a display component: i) attached to, ii) integral with, or iii) configured to be attached to, the attachment component, wherein the display component comprises a display screen, and wherein the display screen displays: i) a tag indicator (e.g., tag schematic) which corresponds to the physical location of a tag (e.g. a tag with an antenna, such as an RFID tag), and ii) at least one of the following additional indictors: A) a total distance indicator which indicates the distance of the device tip to the tag, B) a medical device indicator (e.g., medical device schematic) which corresponds to the location of the medical device with respect to the tag, C) a tag-tip vector indicator which provides a representation of the two-dimensional distance, and two-dimensional location, of the device tip to the tag; and D) a depth indicator which provides an indication of high above, or below, the device tip is with respect to the tag.

In certain embodiments, provided herein are systems and kits comprising: a) a tag, the tag comprising an antenna; b) an attachment component comprising at least one location emitter, wherein the attachment component is configured to be attached to a hand-held medical device with a device tip; and c) a display component attached to, or integral with, (or configured to be attached to) the attachment component, wherein the display component comprises a display screen, and wherein the display screen displays: i) a tag indicator which corresponds to the physical location of the tag, and ii) at least one of the following additional indictors: A) a total distance indicator which indicates the distance of the device tip to the tag, B) a medical device indicator which corresponds to the location of the medical device with respect to the tag, C) a tag-tip vector indicator which provides a representation of the two-dimensional distance, and two-dimensional location, of the device tip to the tag; and D) a depth indicator which provides an indication of high above, or below, the device tip is with respect to the tag.

In certain embodiments, the tag emits sidebands at defined frequencies upon activation by a magnetic field. In other embodiments, the tag indicator is approximately centered on the display screen. In additional embodiments, the display screen further displays a directional indicator which provides information for moving or positioning the medical device. In certain embodiments, the directional indicator comprises an image of the medical device that is distinct from the medical device indicator.

In certain embodiments, the systems and kits further comprise the hand-held medical device. In other embodiments, the attachment component comprising at least two location emitters or at least three location emitters. In further embodiments, the attachment component comprises a sheath that slides over the hand-held medical device. In other embodiments, the attachment component clips or snaps on to the hand-held medical device.

In some embodiments, the kits and systems further comprise a remote activating device that generates a magnetic field within a region of the tag and the at least one location emitter. In certain embodiments, the kits and systems further comprise a plurality of witness stations, each the witness station comprising an antenna configured to detect information: i) emitted from the tag or changes in a magnetic field generated by a remote activating device in response to the tag; and ii) emitted from the at least one location emitter or changes in a magnetic field generated by the remote activating device in response to the at least one emitter.

In additional embodiments, the systems and kits further comprise an electronics component for receiving and process signals from the plurality of witness stations. In other embodiments, the display screen has an area between 3 and 18 square inches (e.g., 3 . . . 6 . . . 9 . . . 12 . . . 15 . . . or 18) or between 9 and 4 square inches. In further embodiments, the display component is moveable with respect to the attachment component such that the display screen may be viewed in different positions (e.g., via a hinged or similar connection).

In certain embodiments, the tag indicator comprises a schematic image of the tag. In further embodiments, the display screen is at least partially see through. In further embodiments, the medical device indicator comprises a schematic image of the hand-held medical device. In some embodiments, the tag-tip vector indicator does not provide depth to tag information. In additional embodiments, the total distance indicator comprises a numerical representation and/or a graphical magnitude symbol. In further embodiments, the depth indicator comprises a numerical and/or graphical magnitude symbol. In other embodiments, the at one of the additional indicators comprises at least two or three of the additional indicator. In further embodiments, the at one of the additional indicators comprises all four of the additional indicators.

In some embodiments, the display screen further displays one or more guides for performing a procedure around the tag (e.g., phantom surgical path). In other embodiments, the one or more guides comprises a plurality of guide rings around the tag indictor (e.g., to allow a circular region around a tag to be cut or excised). In further embodiments, the one or more guides comprises symbols directing a user where or how to move the hand-held medical device to accomplish a task.

In additional embodiments, the tag emits sidebands at frequencies defined by a number programmed into a counter in the tag. In other embodiments, the tag antenna comprises a coil antenna. In some embodiments, the coil antenna comprises a ferrite-core coil antenna. In further embodiments, the coil antenna resonates at 100-200 kHz. In certain embodiments, the coil antenna is coupled to an integrated circuit.

In particular embodiments, the kits and systems further comprise a remote activating device comprising a pad configured to be placed in proximity to a patient having the tag embedded in the patient (e.g., configured to be placed under the patient). In other embodiments, the pad further comprises a plurality of witness stations.

In certain embodiments, the kits and systems further comprise a plurality of witness stations, wherein the plurality of witness stations each comprise a lock-in amplifier tuned to a frequency of a sideband from the tag. In some embodiments, each witness station comprises a plurality of antennas. In other embodiments, each of the witness station antennas feed a receiver channel that is time-division multiplexed. In some embodiments, the plurality of antennas within a witness station are arranged in an orthogonal manner to each other. In particular embodiments, the witness station antennas comprise a ferrite-loaded cylindrical coil antenna tuned for resonance at a frequency of information from the tag.

In some embodiments, the one or more location emitters comprise an antenna, wherein the emitters emits sidebands at defined frequencies upon activation by a magnetic field. In further embodiments, the one or more emitters comprise at least two emitters positioned to permit a plurality of witness stations to detect orientation of the hand-held medical device relative to the tag.

In particular embodiments, the systems and kits further comprise a computer system that receives information from the plurality of witness stations and generates information about the position of the tag. In certain embodiments, the systems and kits further comprise a computer system that receives information from the plurality of witness stations and generates data about the position of the tag and the medical device, and provides the data to the display component.

In particular embodiments, provided herein are methods of identifying a position of a tag, comprising: a) providing the systems or kits described above and herein; b) placing the tag in an object; c) generating a magnetic field with a remote activating device; and d) identifying a position of the tag in the object by collecting information emitted from the tag with a plurality of witness stations to generate data.

In certain embodiments, the methods further comprise providing the data to the display component. In other embodiments, the position comprises relative location of the tag to a medical device. In other embodiments, the position comprises distance of the tag to a the hand-held medical device. In some embodiments, the object is human. In further embodiments, the object is tissue near or in a tumor. In particular embodiments, the methods further comprise the step of conducting a guided surgery using the data. In other embodiments, the identifying comprises displaying the tag indicator on the display screen. In certain embodiments, the identifying further comprises displaying at least one of the total distance indicator, the medical device indicator, the tag-tip vector indicator, and/or the depth indicator on the display screen. In particular embodiments, the identifying further comprises displaying all of the total distance indicator, the medical device indicator, the tag-tip vector indicator, and the depth indicator on the display screen.

In some embodiments, the systems and methods comprise a plurality of components. In some embodiments, a first component comprises one or more tags (which may be used interchangeably with the term "marker") whose location, position, distance, or other properties are to be assessed. In some embodiments, the tags are configured to be positioned in a subject at a surgical location or other clinically relevant location to mark a target region within a body. In some embodiments, a second component comprises a remote activating device that generates a magnetic field. In some embodiments, the second component is located in a device positioned near (e.g., below) a subject containing the one or more tags. In some embodiments, the third component comprises a plurality of witness stations configured to receive a signal generated by the one or more tags upon being exposed to the magnetic field generated by the second component. In some embodiments, the second and third components are physically contained in the same device. In some embodiments, a fourth component comprises a medical device location emitter. The fourth component can be integrated into a medical device or attached or otherwise associated with a medical device. The fourth component comprises one or more emitters (e.g., antennas that emit signals or other types of emitters) that generate signals upon exposure to the magnetic field generated by the second component, said signals detectable by the third component. In some embodiments, a fifth component comprises a computing device comprising a processor that receives information from the witness stations of the third component and generates information about the relative locations, distances, or other characteristics of the tags, the medical device, and the witness stations. In some embodiments, the fifth component comprises a display that displays such generated information to a user of the system.

In some embodiments, the first component is a single tag. In some embodiments, it is two or more tags (e.g., 3, 4, 5, 6, 7, 8, 9, 10, 11, 12, etc.). In some embodiments, where more than one tag is employed, the tags are of identical type while in other embodiments they are of different type.

In some embodiments, the tag comprises a ferrite-core coil antenna (e.g., resonant at 100-200 kHz) coupled to an integrated circuit (IC), which is powered by an AC magnetic field at resonance. In some embodiments, the core is contained in an enclosure (e.g., a cylindrical glass or plastic housing). The AC magnetic field originates from the second component. The exciter antenna(s) is/are driven by a conventional oscillator and power amplifier at a level sufficient to power the tag(s). In some embodiments, the implanted tag amplitude-modulates (AM's) the continuous wave (CW) carrier power from the exciter, thus emitting sidebands at frequencies defined by a number programmed into the tag's counter. In some embodiments, these sidebands, as well as the much stronger CW carrier, are ultimately detected by the third component. In some embodiments, the tag comprises a self-resonant object (e.g., a small ferrite core with a wound inductor). The wound inductor possesses inter-winding capacitance that in combination with the inductance produces a high frequency resonant circuit. In some embodiments, the tag comprises a resonant object (e.g., the self-resonant object is equipped with a chip capacitor to produce resonance at a prescribed frequency). In some embodiments, the tag comprises a resonant or self-resonant object with a diode. A diode in combination with an LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). In some embodiments, detection occurs similar to a full duplex (FDX) radio frequency identification (RFID) except that the modulation pattern is a simple sub-harmonic rather than a coded binary pattern; in some embodiments, the detection occurs after excitation similar to a half-duplex (HDX) mode of operation.

In some embodiments, the tag is configured for single-use. In some such embodiments, a tag can be disabled or deactivated (e.g., like an Electronic Article Surveillance tag (EAS tag)). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the tag has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, ..., etc.), the width is 5 mm or less (e.g., 4 mm or less, ..., 3 mm or less, ..., 2 mm or less, ..., 1 mm or less, ... 0.5 mm or less, ..., etc.), and the depth is 5 mm or less (e.g., 4 mm or less, ..., 3 mm or less, ..., 2 mm or less, ..., 1 mm or less, ... 0.5 mm or less, ..., etc.).

In some embodiments, the tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, ..., 10 mm or less, ..., 9 mm or less, ..., 8 mm or less, ..., 5 mm or less, ..., 3 mm or less, ..., etc.), the width is 5 mm or less (e.g., 4 mm or less, ..., 3 mm or less, ..., 2 mm or less, ..., 1 mm or less, ... 0.5 mm or less, ..., etc.), and the depth is 5 mm or less (e.g., 4 mm or less, ..., 3 mm or less, ..., 2 mm or less, ..., 1 mm or less, ... 0.5 mm or less, ..., etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the tag in place, avoiding migration in tissue. These struts may deploy upon placement in tissue. In some embodiments the fastener may be a biocompatible material that bonds with surrounding tissue.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.).

In some embodiments, the tag does not comprise any power source. For example, in some embodiments, the signal is generated from the signal source in response to a magnetic field as the activation event (i.e., electromagnetic induction).

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the second component (or other device) and then acts as a passive transponder to emit microwaves or UHF radio waves. In some embodiments, the RFID chip is read-only. In other embodiments, it is read/write. The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (e.g., after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, the second component provides a remote activating device having an excitation coil. In some embodiments, the excitation coil is provided in a patch or pad that is placed on the patient or on the operating table, although it can be positioned in any desired location within functional distance of the tags. In some embodiments, the remote activating device provides an AC magnetic field originating from one or more exciter antennas. In some embodiments, where the system is used to locate breast tumors, the patch encircles the treated breast or is placed otherwise near the breast. Similar approaches may be used for other targeted areas of a body. In some embodiments, a pad containing the excitation coil is placed beneath the patient. In such embodiments, a large coil or multiple coils are employed. The excitation coil(s) may comprise or consist of several turns of a flat conductor patterned on a dielectric substrate, or may comprise or consist of magnet wire wound around a suitable mandrel; the coil is powered by an external frequency source, and the magnetic field emanating from the coil penetrates the patient's body to excite the tag, whose emissions are detected by a detection component.

In some embodiments, the excitation coil or coils are contained in a belt that is placed around the subject or a portion of the subject. In some embodiments, the external excitation coil may further be used for other aspects of the patient care, such as for radiotherapy or to act as a ground current return pad used in electrosurgery. In some embodiments, the remote activating device emits light (e.g., laser light). In some embodiments, the remote activating device is configured for single use (e.g., is disposable).

In some embodiments, the remote activating device employs an unmodulated constant frequency activation (i.e., the activation signal has constant amplitude and frequency). In some embodiments, the remote activating device employs an unmodulated swept frequency (i.e., the activation signal has constant amplitude and swept frequency between two endpoints). Such devices find use with resonant-type tags such that a detectable change in the activation signal's amplitude occurs when the transmitted frequency coincides with the tag's resonant frequency. In some embodiments, the remote activating device employs a pulsed frequency (i.e., the activation signal comprises brief excitation pulses at a periodic frequency, which may be comprised of two closely-related frequencies whose sum or difference is the response frequency of the tag). The pulsed activation produces a post-pulse sinusoidal decay signal. A tag alters the characteristic of the decaying signal, either in amplitude or time.

In some embodiments, the remote activating device comprises a hand-held component. In some embodiments, the hand-held component is lightweight to allow a surgeon to hold and manipulate the component over the course of a procedure (e.g., 5 kg or less, 4 kg or less, 3 kg or less, 2 kg or less, 1 kg or less, 0.5 kg or less, 0.25 kg or less, or any range therein between, e.g., 0.5 to 5 kg, 1 to 4 kg, etc.). In some embodiments, the hand-held component is shaped like a wand, having a proximal end that is held by the physician and a distal end that is pointed towards the treated subject or tissue harboring the tag. In some embodiments, the hand-held component is shaped like an otoscope, having a distal end that terminates at an angle (e.g., right angle) from the body of the component. In some embodiments, the remote activating device comprises an antenna that generates a magnetic field. In some embodiments, the remote activating device has only a single antenna (i.e., is monostatic). In some embodiments, the remote activating device has only two antennas (i.e., is bistatic).

In some embodiments, the magnetic field of the remote activating device is controlled by a processor running a computer program. In some embodiments, the remote activating device comprises a display or user interface that allows the user to control the remote activating device and/or monitor its functions while in use. In some embodiments, the remote activating device provides a visual, audio, numerical, symbol (e.g., arrows), textual, or other output that assists the user in locating the tag or identifying the distance to or direction of the tag from the remote activating device.

In some embodiments, the plurality of witness stations of the third component collectively provide several antennas at multiple defined locations relative to the tags and configured to receive a signal generated by the one or more tags upon being exposed to the magnetic field generated by the second component.

In some embodiments, each receiving antenna feeds a receiver channel, which is time-division multiplexed (TDM'd) to reduce the receiver complexity. Fixed witness stations of defined locations relative to the tag and each other (e.g., arrayed along the patient) contain one or more (e.g., one to three) witness antennas arranged in a locally orthogonal manner to sense various components of the AC magnetic field from the tag. In some embodiments, one or more or all of these witness antennas in the witness stations is also TDM'd into a receiver channel, reducing complexity, as well as cross-talk between antennas.

In some embodiments, witness antennas comprise or consist of a ferrite-loaded cylindrical coil antenna, tuned (e.g., with one or more capacitors in parallel) for resonance at the frequency of an exciter (e.g., tag or emitter), (e.g., 100-200 kHz). Typical dimensions of a witness antenna are 3-5 mm diameter and 8-12 mm length, although both smaller and larger dimensions may be employed.

In some embodiments, the witness stations are provided below the patient (e.g., in a pad, garment, or other device positioned below the patient). In some embodiments, the witness stations are integrated into a surgical table or imaging device in which a patient is placed during a medical procedure. In some embodiments, the witness stations are placed on the floor, wall, or ceiling of the operating room or in a medical transport vehicle. In some embodiments, the witness stations are integrated into or attached to a medical device used in the medical procedure.

In some embodiments, a fourth component provides a medical device location emitter to allow the system to determine the location, position, distance, or other characteristic of a medical device relative to the tag or tags. In some embodiments, the medical device location emitter or emitters are integrated into a medical device. In other embodiments, they are attachable to a medical device. In some such embodiments, the emitters are provided in a sleeve that slips over a portion of a medical device. The emitters may operate as and/or comprise the same materials as the tags, but are positioned on or near a medical device rather than within tissue. For example, in some embodiments, the emitters comprise coils that are excited with both carrier and/or sidebands, enabling the emitters to emit signals as though it were a tag.

In some embodiments, location of the emitters is accomplished geometrically by measuring the quasi-simultaneous power detected from the emitters at a plurality of witness stations (e.g., four or more stations), and using the power differences to perform vector math that determines the location of the emitter without ambiguity. This process is facilitated by a preliminary calibration using a known tag in a known location prior to the procedure. Vectors describing the location of emitters are used to provide visualization guidance to the surgeon about the spatial relationship of a medical device (e.g., particularly its tip) to an implanted tag, or (e.g., with computational guidance) to a lesion boundary. Use of multiple emitters on a medical device provides vectors to determine the device's principal axis using the same vector math. Where a more complex medical device, such as a robotic surgical system (e.g., da Vinci surgical system) is employed, multiple emitters located on multiple different locations of the device are employed to provide location, orientation, and other position information of multiple components (e.g., arms) of the device.

In some embodiments, the emitters are also used as detectors (e.g., provide witness stations on the medical device).

In some embodiments, a fifth component provides one or more computing systems comprising one or more computer processors and appropriate software to analyze, calculate, and display tag and emitter position information. In some embodiments, the display provides a graphical representation of the tag, patient, and/or medical device on a monitor. In other embodiments, the display provides directional information for moving or positioning the medical device. In some embodiments, the system automatically (e.g., robotically) controls the medical device or one or more functions thereof. In some embodiments, the display integrates tag and/or medical device information with previously obtained or concurrently obtained medical images of the patient or target tissue (e.g., CT, MRI, ultrasound, or other imaging modalities). For example, in some embodiments, an image indicating a tag or tags is fused with an image of the subject's tissue or body region obtained from an imaging device. In some embodiments, information is analyzed in real-time. In some embodiments, information is analyzed at one or more discrete time points.

In some embodiments, the fifth component provides command and control functions for a user of the system. In some embodiments, the fifth component has information stored thereon that helps guide the information displayed on the detection component. For example, the information may include data on the type of medical device the detection component is attached to, or what tip or cutting implement is being used with a particular medical device. In this regard, the precise location of the cutting tip of a medical device and its relation to the tag (e.g., distance to the tag) is communicated to the surgeon (e.g., for very precise instructions on cutting tissue). Such information is, for example in some embodiments, manually entered into a control unit or detection component by the user, or automatically found (e.g., by a barcode or other indicator) when a detection component is attached to a particular medical device.

The system finds use with a wide variety of medical devices and procedures. In some embodiments, the surgical device comprises an electrical surgical device that is turned on and off by a user, wherein a control unit that is part of the fifth component allows the remote activating device to generate the magnetic field when the electrical surgical device is off, and prevents the remote activating device from generating the magnetic field when the electrical surgical device is on (e.g., ensuring that the surgical device and detection system do not interfere with one another). In other embodiments, the surgical device comprises a power cord, wherein an AC current clamp is attached to the power cord, wherein the AC current clamp is electrically-linked or wirelessly linked to the control unit, wherein the AC current clamp senses when the electrical surgical device is on or off and reports this to the control unit (e.g., such that the control unit can ensure that the magnetic field from the surgical device and from the remote activating device are not active at the same time).

In certain embodiments, the surgical device comprises an electrocautery device, a laser cutting device, a plasma cutting device, or a metal cutting device (e.g., a surgical device manufactured by BOVIE MEDICAL). Additional examples of medical devices that find use in embodiments of the system are found, for example, in the following U.S. Pat. Nos.: 9,144,453; 9,095,333; 9,060,765; 8,998,899; 8,979, 834; 8,802,022; 8,795,272; 8,795,265; 8,728,076; 8,696, 663; 8,647,342; 8,628,524; 8,409,190; 8,377,388; 8,226, 640; 8,114,181; 8,100,897; 8,057,468; 8,012,154; 7,993, 335; 7,871,423; 7,632,270; 6,361,532; all of which are herein incorporated by reference in their entireties, and particularly with respect to the hand-held medical devices disclosed therein.

In some embodiments, the medical device has thereon (e.g., provided as part of the fourth component) an indicator for directing the surgeon to the tag or tags. In some embodiments, the indicator provides: i) a spatial orientation indicator (e.g., visual, audible, etc.), and/or ii) a distance-to-tag indicator (e.g., visual, audible, etc.). In some embodiments, the indicator comprises a first display for presenting distance to tag information (e.g., visual, audible, lights, color, vibration, tactile, etc.), a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the indicator comprises a plurality of displays (e.g., visual, audible, sensory, etc.) that allow the correct pitch and yaw axes to be employed (to minimize non-target tissue damage), and/or further a display that provides distance to tag information.

In certain embodiments, the medical device is moved around the patient's body prior to surgery (e.g., open surgery or percutaneous surgery) to orient the emitters and the indicator component. In certain embodiments, a series of lights and/or sounds is provided on the indicator that guides the surgeon (e.g., the surgeon attempts to keep the lights in a center of an "X" series of lights, and/or to keep the volume of warning sounds off or as low as possible).

The tag is not limited to placement within a particular body region, body part, organ, or tissue. For example, in some embodiments, the tag is placed in the cephalic, cervical, thoracic, abdominal, pelvic, upper extremities, or lower extremities region of the body. In some embodiments, the tag is placed within an organ system, such as the skeletal system, muscular system, cardiovascular system, digestive system, endocrine system, integumentary system, urinary system, lymphatic system, immune system, respiratory system, nervous system or reproductive system. In some embodiments, the tag is placed within an organ. Such organs may include the heart, lungs, blood vessels, ligaments, tendons, salivary glands, esophagus, stomach, liver, gallbladder, pancreas, intestines, rectum, anus, hypothalamus, pituitary gland, pineal gland, thyroid, parathyroids, adrenal glands, skin, hair, fat, nails, kidneys, ureters, bladder, urethra, pharynx, larynx, bronchi, diaphragm, brain, spinal cord, peripheral nervous system, ovaries, fallopian tubes, uterus, vagina, mammary glands, testes, vas deferens, seminal vesicles, and prostate. In some embodiments, the tag is placed within tissues, such as connective, muscle, nervous, and epithelial tissues. Such tissues may include cardiac muscle tissue, skeletal muscle tissue, smooth muscle tissue, loose connective tissue, dense connective tissue, reticular connective tissue, adipose tissue, cartilage, bone, blood, fibrous connective tissue, elastic connective tissue, lymphoid connective tissue, areolar connective tissue, simple squamous epithelium, simple cuboidal epithelium, simple columnar epithelium, stratified epithelium, pseudostratified epithelium, and transitional epithelium.

In some embodiments, the tissue region where the tag is located comprises a lesion. In some embodiments, the lesion is a tumor or a tissue region identified as being at risk for forming a tumor. In some embodiments, the lesion is fibrotic tissue. In some embodiments, the lesion is an inflamed or infected region. In some embodiments, the tag is placed within a lumen to detect function or other process of the organ or provide localizing information. For example, the tag could be swallowed, or placed into a hollow organ via endoscopy. In some embodiments, the tissue region is healthy tissue.

In some embodiments, the tag is placed within a solid tumor. Examples of solid tumors into which the tag may be placed include carcinomas, lymphomas, and sarcomas, including, but not limited to, aberrant basal-cell carcinoma, acinar cell neoplasms, acinic cell carcinoma, adenocarcinoma, adenoid cystic carcinoma, adenoid/pseudoglandular squamous cell carcinoma, adnexal neoplasms, adrenocortical adenoma, adrenocortical carcinoma, apudoma, basal cell carcinoma, basaloid squamous cell carcinoma, carcinoid, cholangiocarcinoma, cicatricial basal-cell carcinoma, clear cell adenocarcinoma, clear cell squamous-cell carcinoma, combined small cell carcinoma, comedocarcinoma, complex epithelial carcinoma, cylindroma, cystadenocarcinoma, cystadenoma, cystic basal-cell carcinoma, cystic neoplasms, ductal carcinoma, endometrioid tumor, epithelial neoplasms, extramammary Paget's disease, familial adenomatous polyposis, fibroepithelioma of Pinkus, gastrinoma, glucagonoma, Grawitz tumor, hepatocellular adenoma, hepatocellular carcinoma, hidrocystoma, Hurthle cell, infiltrative basal-cell carcinoma, insulinoma, intraepidermal squamous cell carcinoma, invasive lobular carcinoma, inverted papilloma, keratoacanthoma, Klatskin tumor, Krukenberg tumor, large cell keratinizing squamous cell carcinoma, large cell nonkeratinizing squamous cell carcinoma, linitis plastica, liposarcoma, lobular carcinoma, lymphoepithelial carcinoma, mammary ductal carcinoma, medullary carcinoma, medullary carcinoma of the breast, medullary thyroid cancer, micronodular basal-cell carcinoma, morpheaform basal-cell carcinoma, morphoeic basal-cell carcinoma, mucinous carcinoma, mucinous cystadenocarcinoma, mucinous cystadenoma, mucoepidermoid carcinoma, multiple endocrine neoplasia, neuroendocrine tumor, nodular basal-cell carcinoma, oncocytoma, osteosarcoma, ovarian serous cystadenoma, Paget's disease of the breast, pancreatic ductal carcinoma, pancreatic serous cystadenoma, papillary carcinoma, papillary hidradenoma, papillary serous cystadenocarcinoma, papillary squamous cell carcinoma, pigmented basal-cell carcinoma, polypoid basal-cell carcinoma, pore-like basal-cell carcinoma, prolactinoma, pseudomyxoma peritonei, renal cell carcinoma, renal oncocytoma, rodent ulcer, serous carcinoma, serous cystadenocarcinoma, signet ring cell carcinoma, signet-ring-cell squamous-cell carcinoma, skin appendage neoplasms, small cell carcinoma, small cell keratinizing squamous cell carcinoma, somatostatinoma, spindle cell squamous cell carcinoma, squamous cell carcinoma, squamous cell lung carcinoma, squamous cell thyroid carcinoma, superficial basal-cell carcinoma, superficial multicentric basal-cell carcinoma, syringocystadenoma papilliferum, syringoma, thymoma, transitional cell carcinoma, verrucous carcinoma, verrucous squamous cell carcinoma, VIPoma, and Warthin's tumor.

In some embodiments, placing the tag comprises the steps of inserting an introduction device into the subject and introducing the tag through the introduction device into the subject. In some embodiments, the introduction device is a needle, cannula, or endoscope. In some embodiments, the tag is forced through the introduction device (e.g., via physical force, pressure, or any other suitable technique) and released into the subject at the distal end of the introduction device. After the tag is placed, the introduction device is withdrawn, leaving the tag at the desired location with the subject. In some embodiments, the introduction of the tag is guided by imaging technology.

In some embodiments, multiple tags are placed into the subject. The tags may be of identical type or may differ (e.g., differ in signal type). The tags may be placed in proximity to one another or at distant locations. Multiple tags are used, in some embodiments, to triangulate the location intended for medical intervention.

In some embodiments, the tags are further used as fiducials for radiotherapy (or other targeted therapy). The location of the tags is identified with an external reader and used to place, for example, laser light on the skin surface exactly where the chip is located. This eliminates the need to use X-ray, CT, or fluoroscopy to see the fiducials. This also decreases or eliminates the need to put skin markers (e.g., tattoos) on patients. This also helps in respiratory compensation as the fiducial moves up and down with a tumor in the lung or abdomen. Therefore, one can conduct real-time radiation only when the tumor is in the correct position and decrease damage to the background tissue (e.g., avoid burning a vertical stripe in the patient as the tumor moves up and down). The use as fiducials for director therapy (e.g., radiation therapy) also enhances triangulation as depth information (based on signal strength) assists in localization of the tumor to minimize collateral damage.

In some embodiments, provided herein are systems and methods employing one or more or all of: a) a tag (e.g., comprising an antenna; e.g., a coil antenna; e.g., a ferrite-core coil antenna; e.g., that resonates at 100-200 kHz; e.g., coupled to an integrated circuit); b) a remote activation device that generates a magnetic field within a region of the tag; and c) a plurality of witness stations, each of the witness stations comprising an antenna configured to detect information generated by said tag or a change in a magnetic field generated by the remote activation device caused by said tag. In some embodiments, the tag emits sidebands at defined frequencies upon activation by a magnetic field and the witness stations detect such sidebands. In some embodiments, the tag emits the sidebands at frequencies defined by a number programmed into a counter in the tag.

In some embodiments, the remote activating device comprises an excitation coil that is, for example, powered by a generator electrically connected to the remote activating device. In some embodiments, the remote activating device comprises a pad configured to be placed in proximity to (e.g., under, above, beside) a patient having the tag embedded in the patient. In some embodiments, the pad also contains the witness stations.

In some embodiments, the witness stations are tuned to a frequency of the sidebands. In some embodiments, each witness station comprises a plurality of antennas. In some embodiments, each witness station antenna feeds a receiver channel that is time-division multiplexed. In some embodiments, each antenna of a plurality of antennas within a witness station is arranged in an orthogonal manner to each other. In some embodiments, the witness station antennas comprise a ferrite-loaded cylindrical coil antenna tuned for resonance at a frequency of the signals to be detected (e.g., from a tag or emitter).

In some embodiments, the system further comprises one or more emitters configured for attachment to a medical device. Any type of attachment may be employed. The one or more emitters may be integrated with the device or may be added to the devices (e.g., via on an attachment component, such as a sheath, that slides over a portion of the device). In some embodiments, the emitters are designed similarly to the tag. For example, in some embodiments, the one or more emitters comprise an antenna, wherein the emitters emit sidebands at defined frequencies upon activation by a magnetic field. In some embodiments, the one or more emitters comprise at least two emitters positioned to permit the witness stations to detect orientation of said medical device relative to the tag.

In some embodiments, the system further comprises a computer system that receives information from the plurality of witness stations and generates information about the position of the tag and/or the medical device. In some embodiments, the system further comprises a display that displays the generated information to a user. In some embodiments, the display is on a monitor or on a medical device.

In some embodiments, provided herein are systems and methods comprising: a) a tag; b) an emitter attached to a medical device; c) a remote activation device that generates a magnetic field within a region of the tag and the emitter; and d) a plurality of witness stations, each said witness station comprising an antenna configured to detect information: i) emitted from the tag or changes in a magnetic field generated by the remote activating device in response to the tag; and/or ii) emitted from the emitter or changes in a magnetic field generated by the remote activating device in response to the emitter.

Also provided herein are uses of any of the above systems (e.g., for detecting a position of a tag in an object; for detecting a position of a tag relative to a medical device; etc.).

Further provided herein are methods of identifying a position of a tag, comprising: a) providing any of the systems described herein; b) placing the tag in an object; c) generating a magnetic field with the activating device; and d) identifying a position of said tag in said object by collecting information emitted from the tag with the witness stations. In some embodiments, the position or comprises relative location or distance of the tag to a medical device.

In particular embodiments, provided here are devices, kits, or systems comprising: a hand-held medical device that is attached to or integral with a display component, wherein the display component comprises a display screen. In some embodiments, the hand-held medical device comprises an electrocautery hand-held surgical tool. In other embodiments, electrocautery hand-held surgical device comprises a BOVIE cautery device or similar device. In further embodiments, the display screen is in a user's line of sight when using said hand-held medical device to perform a procedure.

Definitions

As used herein, the terms "processor" and "central processing unit" or "CPU" are used interchangeably and refer to a device that is able to read a program from a computer memory (e.g., ROM or other computer memory) and perform a set of steps according to the program.

As used herein, the terms "computer memory" and "computer memory device" refer to any storage media readable by a computer processor. Examples of computer memory include, but are not limited to, RAM, ROM, computer chips, digital video discs (DVD), compact discs (CDs), hard disk drives (HDD), optical discs, and magnetic tape. In certain embodiments, the computer memory and computer processor are part of a non-transitory computer (e.g., in the control unit). In certain embodiments, non-transitory computer readable media is employed, where non-transitory computer-readable media comprises all computer-readable media with the sole exception being a transitory, propagating signal.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject/patient suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiments, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

DESCRIPTION OF DRAWINGS

FIG. 10A (side view) and FIG. 10B (top view) show an attachment component 10 attached to a medical device 20, having a distal tip 25, where a human hand is holding the medical device +attachment component combination. The attachment component 10 has one, two, three or more location emitters 70 therein (not pictured; see FIG. 6), which allows the three-dimensional orientation of the medical device 20 and device tip 25 to be determined relative to the tag 100 and displayed on display component 40. FIG. 10C shows a display component 40 that includes a display screen 45, which displays: 1) a total distance indicator 80; 2) a tag indicator (e.g., schematic image, symbol, dot, circle, etc.) 101 that corresponds to the location of the actual tag 100; 3) a medical device indicators (e.g., schematic image, line, etc.) 21 and device tip indicator (e.g., schematic image, line, circle, etc.) 26, which correspond to the actual medical device 20 and device tip 25; 4) a tag-tip vector indicator (e.g., broad line, skinny line, tapered shape, etc.) 85, which extends from the tag indicator (e.g., schematic image) 101 to the device tip indicator (e.g., image) 26; and 5) a depth indicator 90, which provides a visual indicator of how high above or below the device tip 25 is compared to the tag 100.

FIG. 11 shows the same components as FIG. 10, showing how all of the following move or change on the display screen 45 when the medical device 25 with attached attachment component 10 are moved by a human hand to a different position than in FIG. 10: the tag indicator (e.g., schematic image) 101, tag-tip vector indicator 85, device tip indicator 26, medical device indicator 21, total distance indicator 80, and depth indicator 90.

FIG. 12 shows the same components as FIGS. 10 and 11, and shows how all of the following move or change on the display screen 45 when the device tip 25 is hovered 29 mm directly over the tag 100: the tag indicator (e.g., schematic image) 101, tag-tip vector indicator 85, device tip indicator 26, medical device indicator 21, total distance indicator 80, and depth indicator 90.

FIG. 13 shows the same components as FIGS. 10-12, and shows the device tip 25 at, or very close, to zero mm's above the tag, which is shown visually on the display screen 45 as a large peak on the depth indicator 90.

FIG. 14 shows the same components as FIGS. 10-13, but shows the total distance indicator 80 near the device tip image 26, rather than in the lower right hand corner of the display screen 45. FIG. 14 also shows a plurality of guide rings 95 centered on the tag indicator (e.g., schematic image) 101, which provide, for example, a set distance from the tag 100 (e.g., allowing a surgeon to use these as guides for cutting tissue).

FIG. 15 shows the same components as FIG. 14, where the device tip 25 has been moved to be centered over the tag 100, thereby causing the tag indicator (e.g., schematic image) 101 to light up brighter, providing a visual signal to a user that the device tip 25 is centered over the tag 100.

DETAILED DESCRIPTION

Figure 1:
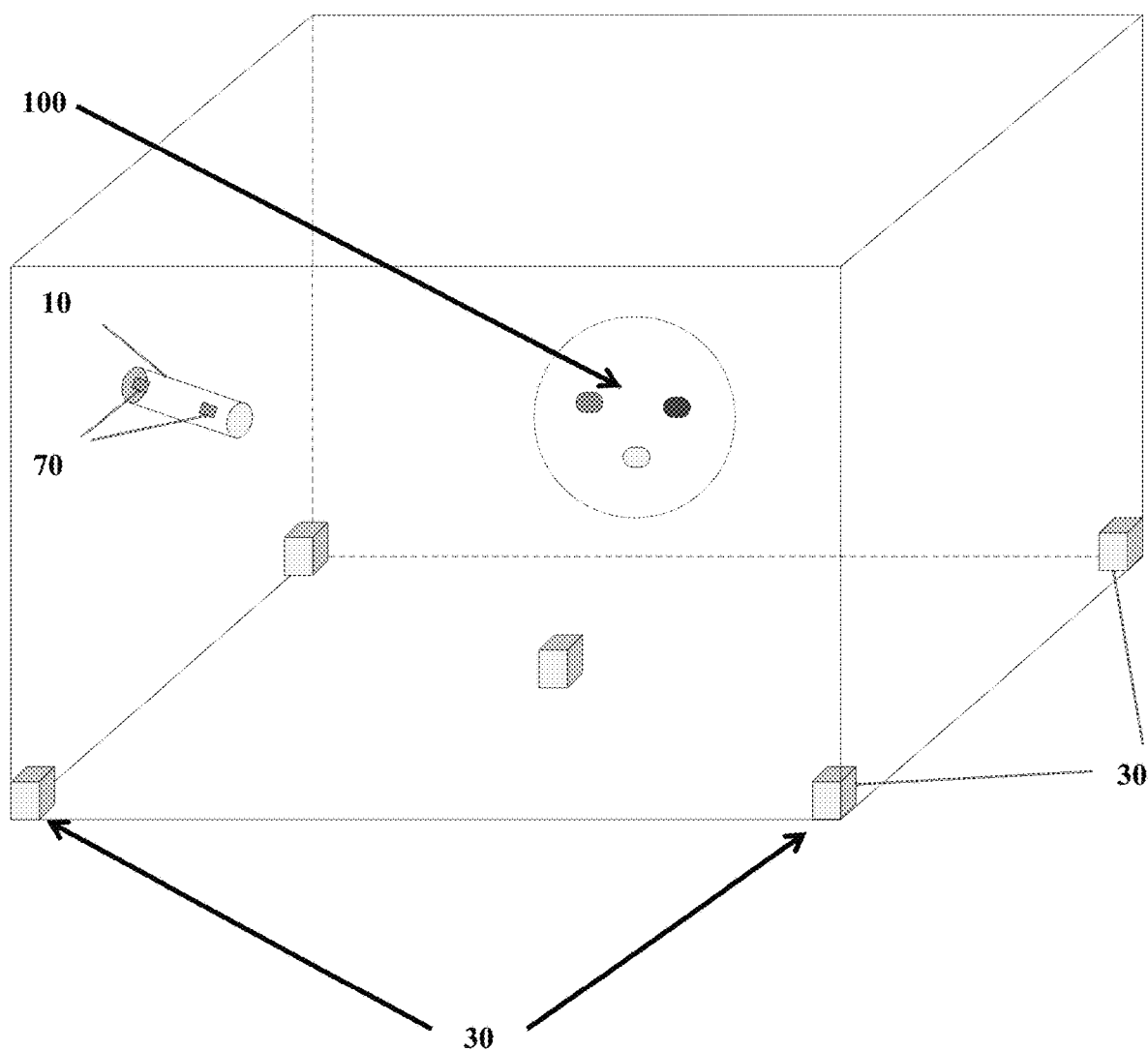
FIG. 1 shows an exemplary 3-dimensional positioning of tags, witness stations, and locator emitters on an attachment component (e.g., wand, sheath, or clip on device) configured to fit over or onto a medical device.

Provided herein are systems, devices, assemblies, and methods for localization a tag, for example, in a tissue of a patient. For example, provided herein are systems, devices, and methods employing one or more or all of: a) one or more tags placed into an object, such as a patient; b) a remote activating device that generates an electromagnetic field within a region of the one or more tags; c) a plurality of witness stations that receive information from the one or more tags that have been exposed to the electromagnetic field; d) one or more emitters positioned on a medical device that are exposed to the electromagnetic field and that emit information received by the witness stations; and e) a computer system for analyzing information received by the witness station and generating and displaying information about the positions of the medical device and/or tag or tags (e.g., relative location, relative distance, orientation, etc.).

The systems and methods may be used in any context where the position of a tag is desired and/or where the relative position of another device (e.g., a medical device) is relative to a tag or tags. While the specification focuses on medical uses in human tissues, it should be understood that the systems and methods find broader use, including non-human uses (e.g., use with non-human animals such as livestock, companion animals, wild animals, or any veterinary settings). For example, the system may be used in environmental settings, agricultural settings, industrial settings, or the like.

In some preferred embodiments, the tag comprises a coil antenna. In some embodiments, the coil antenna is a ferrite-core coil antenna. In some embodiments, the coil antenna resonates at 100-200 kHz. In some embodiments, the coil antenna is coupled to an integrated circuit (IC). In some embodiments, the IC is powered by an AC magnetic field at resonance (e.g., provided by an activating device). In some embodiments, the coil antenna is provided in an enclosure (e.g., a glass or plastic enclosure). In some embodiments, the tag (with enclosure, if present) has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). In some embodiments, the tag, with enclosure, is shaped as an approximately 2×4 mm cylinder or smaller. In some embodiments, the tag amplitude-modulates (AM's) the continuous wave (CW) carrier power from the magnetic field from the activating device, thus emitting sidebands at frequencies defined by a number programmed into the tag's counter. These sidebands, as well as the much stronger CW carrier if desired, are detected for the purpose of analyzing the position of the tag. The use of side bands permits a corresponding detector or detectors (e.g., witness stations) to detect the specific signal from the tag (e.g., using a lock-in amplifier tuned to the side band), without detecting background noise. This allows for precise, real-time detection and analysis of one or more tags, including analysis of relative position and distance from another object (e.g., a medical device).

Any number of other tag designs may be employed. In some embodiments, the tag comprises or consists of a ferrous pellet or particle. When the ferrous object is introduced within a magnetic field, the object creates an irregularity in the alternating magnetic field which is detectable by sense coils contained within witness stations, producing a phase and amplitude shift from null. The null is restored when the ferrous object is physically equidistant to two sense coils.

In some embodiments, the tag comprises a self-resonant object (e.g., a small ferrite core with a wound inductor). The wound inductor possesses inter-winding capacitance that in combination with the inductance produces a high frequency resonant circuit. Detection occurs, for example, using the approach described above for the ferrous pellet or, for example, using a Grid Dip Oscillator (GDO). The GDO has a resonant circuit that radiates an electromagnetic field. When proximal to the self-resonant object of the same frequency, power transfer from the GDO to the self-resonant object induces a detectable change in the GDO power. In some embodiments, the tag comprises a resonant object (e.g., self-resonant object is equipped with a chip capacitor to produce resonance at a prescribed frequency). In some embodiments, the tag comprises a resonant or self-resonant object with a diode. A diode in combination with LC circuit produces a sub-harmonic frequency when immersed in a magnetic field of sufficient strength (imposed voltage exceeds the diode's band-gap potential). In some embodiments, the tag comprises a resonant object or self-resonant object with an active modulator (e.g., integrated circuit amplitude modulates resonant circuit). Detection occurs similar to a full duplex (FDX) radio frequency identification (RFID) except that the modulation pattern is a simple sub-harmonic rather than a coded binary pattern.

In some embodiments, the tag comprises a radio-frequency identification (RFID) chip (e.g., in a housing). In some embodiments, the RFID chip comprises a radio-frequency electromagnetic field coil that modulates an external magnetic field to transfer a coded identification number and/or other coded information when queried by a reader device. In some embodiments, the RFID chip collects energy from an EM field generated by the activating device (or other device) and then acts as a passive transponder to emit microwaves or UHF radio waves. In some embodiments, a reader (which can be part of the activation device or another device) sends a signal to the RFID chip and reads its response. In some embodiments, the RFID chip is read-only. In other embodiments, it is read/write. The technology is not limited by the nature of the information provided by the RFID chip. In some embodiments, the information includes a serial number, lot or batch number, time information (e.g., production date; surgery date; etc.); patient-specific information (e.g., name, family history, drugs taken, allergies, risk factors, procedure type, gender, age, etc.); procedure-specific information; etc. The technology is not limited by the frequency used. In some embodiments, the RFID frequency is in the 120-150 kHz band (e.g., 134 kHz), the 13.56 MHz band, the 433 MHz band, the 865-868 MHz band, the 902-928 MHz band, the 2450-5800 MHz band, or the like. In some embodiments, the RFID chip is incorporated with browser-based software to increase its efficacy. In some embodiments, this software allows for different groups or specific hospital staff, nurses, and patients to see real-time data relevant to the tag, procedure, or personnel. In some embodiments, real-time data is stored and archived to make use of historical reporting functionality and to prove compliance with various industry regulations. In some embodiments, the RFID chip reports sensor data (e.g., temperature, movement, etc.). In some embodiments, the RFID chip contains or collects information that is read at a later time (e.g., after surgery). In some embodiments, information is reviewed during surgery. For example, a message may be provided to the surgeon (e.g., "the chip is just to the left of the tumor") to assist in guiding the surgeon (e.g., optimizing removal of a tumor with the appropriate margins).

In some embodiments, the tag consists of or consists essentially of the signal source and the housing or the signal source, the housing, and the RFID chip. In some embodiments, the tag (e.g., via the chip) emits an ultrasound signal (e.g., gray scale, spectral, or color Doppler) such that the signal is detectable by an ultrasound probe or a hand-held Doppler unit.

In some embodiments, a tag is heated during a procedure (e.g., via exposure to an external energy source). In some such embodiments, heating may be used to assist in coagulation or precoagulation of tissue or to provide thermotherapy (see e.g., U.S. Pat. Publ. No. 2008/0213382, herein incorporated by reference in its entirety). Heating may also be used to improve the efficacy of radiation therapy.

In some embodiments, the tag is configured for single-use. In some such embodiments, a tag can be disabled or deactivated (e.g., like an Electronic Article Surveillance tag (EAS tag)). This is particularly useful where multiple tags are used in a procedure where individual tags are turned off to make detection of other tags easier (e.g., to avoid or reduce interference between multiple tags). In some embodiments, a burst of energy from an external device is used to disable or deactivate a tag. In other embodiments, the tag has an internal control component that, upon receiving instruction from an external device, turns the tag on or off (e.g., the tag stops "talking" temporarily or permanently).

In some embodiments, the localization tag is contained in a housing. In some embodiments, no housing is employed. In some embodiments, the housing comprises a biocompatible material. In some embodiments, the housing provides a liquid and/or gas resistant barrier separating the signal source from the exterior of the housing. In some embodiments, the housing is small, permitting administration of the tag through a needle, cannula, endoscope, catheter, or other medical device. In some such embodiments, the housing has an exterior length, width, and depth, wherein the length is 30 mm or less (e.g., 20 mm or less, . . . , 10 mm or less, . . . , 9 mm or less, . . . , 8 mm or less, . . . , 5 mm or less, . . . , 3 mm or less, . . . , etc.), the width is 5 mm or less (e.g., 4 mm or less, . . . , 3 mm or less, . . . , 2 mm or less, . . . , 1 mm or less, . . . 0.5 mm or less, . . . , etc.), and the depth is 5 mm or less (e.g., 4 mm or less, . . . , 3 mm or less, . . . , 2 mm or less, . . . , 1 mm or less, . . . 0.5 mm or less, . . . , etc.). The housing can be of any desired shape. In some embodiments, the housing is cylindrical along the length axis. In some embodiments, the housing is shaped like a grain of rice (e.g., cylindrical with rounded ends). In some embodiments, the housing is shaped like a pillar (e.g., cylindrical with flat ends). In some embodiments, the housing is polygonal along the length axis (e.g., triangular, square, rectangular, trapezoidal, pentagonal, etc., in cross-section). In some embodiments the housing has struts or other fasteners to keep the device in place, avoiding migration in tissue. These struts may deploy upon placement in tissue. In some embodiments the fastener may be a biocompatible material that bonds with surrounding tissue. In some embodiments, the tag comprises an anti-migration surface. In some embodiments, the anti-migration surface is textured to reduce movement of the tag when in contact with tissue or a target location. The anti-migration feature may be made of any desired material, including, but not limited to titanium, nitinol, polyethylene, terepthalate, nylon, polyethylene, polytetrafluoroethylene, polypropylene, polyurethane, polyamide, silicone, and combinations thereof.

In some embodiments, the housing is a single uniform component synthesized around the interior components of the tag. In other embodiments, the housing is made of two or more separate segments that are sealed together after introduction of the interior components of the tag. In some embodiments, the tag is completely or partially covered in a coating. In some embodiments, the coating comprises a biocompatible material (e.g., parylene-C, etc.). In some embodiments, the tag does not comprise any power source. For example, in some embodiments, the signal is generated from the signal source in response to a magnetic field as the activation event (i.e., electromagnetic induction).

Figure 4:
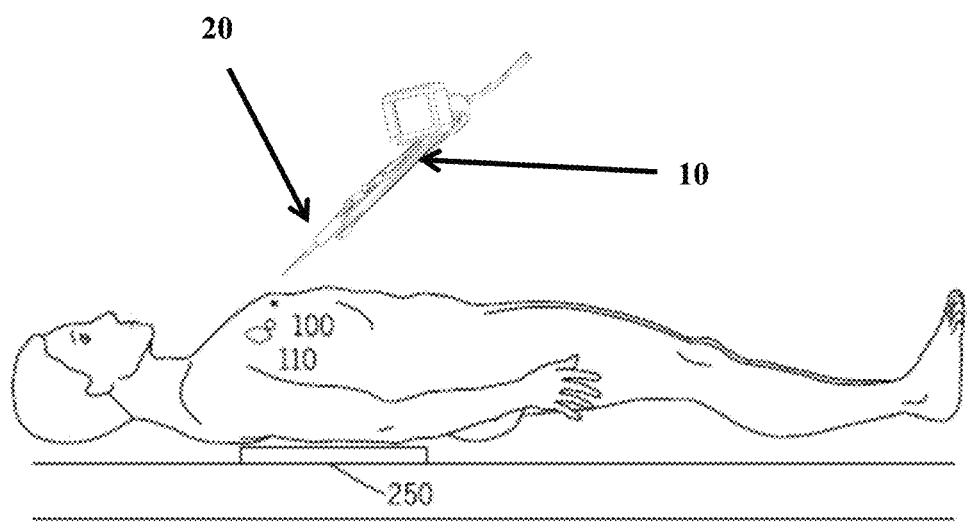
FIG. 4 shows an exemplary positioning of tags, a pad comprising a remote activating device and/or witness stations, and a medical device.
Figure 5:
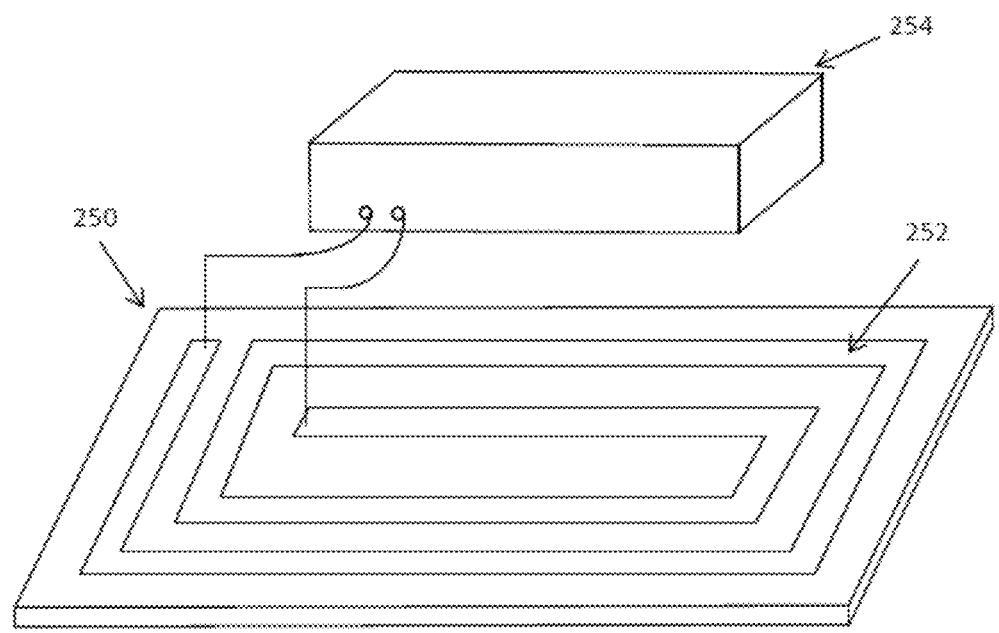
FIG. 5 shows an exemplary power supply connected to excitation coils positioned within a remote activating device.

In some embodiments, the remote activating device comprises one or more excitation coils contained in a flat pad. In some embodiments, the pad is sized and shaped to fit beneath a patient during a medical procedure. The pad may be integrated or placed on a surgical table or imaging system, may be integrated into the patient's clothing, or otherwise placed in the surgical field. FIG. 5 provides exemplary remote activating device 250 containing an excitation coil 252 and connected to a generator 254 by wires. FIG. 4 shows an exemplary placement of the remote activating device 250 between a surgical table and a subject, the subject having a tissue mass (e.g., tumor) 110 and a tag 100 inserted near the tissue mass 110. A medical device 20, that is attached to an attachment component 10 (having one or more location emitters 70 therein) is positioned above the patient. The tag 100 and the medical device 20, and the attachment component 10, are within range of a magnetic field that is generated by the remote activating device 250. In some embodiments, the excitation source of the activation device is a synthesized and stabilized frequency source (e.g., oscillator) whose output is gain-controlled (e.g., via an intermediate amplifier) and provided to a power amplifier to maintain adequate power levels for driving the implanted tag or emitter on a medical device.

In some embodiments, the witness stations are also included in the same device (e.g., pad) as the remote activating device. In other embodiments, they provided in a different device. In some embodiments, witness stations are provided on or associated with a medical device. For example, in some embodiments, a component configured to fit around a medical device that comprises a housing that contains three witness stations that are arrange in a triangle configuration and an electronics component for receiving and processing signals received by the witness stations. The housing has a device-securing opening therein, that allows a medical device to be inserted and secured in place.

In some embodiments, each witness antenna comprises or consists of a ferrite-loaded cylindrical coil antenna, tuned (e.g., with one or more capacitors in parallel) for resonance at the frequency of an exciter (e.g., tag or emitter) (e.g., typically 100-200 kHz). Typical dimensions of a witness antenna are 3-5 mm diameter and 8-12 mm length, although both smaller and larger antenna may be employed. In some embodiments, witness station antenna has a ferrite core size of 0.25×1 inch and contains 75-80 turns of a 10/46 (10 strands of #46) Litz wire which provides 0.157 mH (Q=53) (75 Turns).

Figure 3:
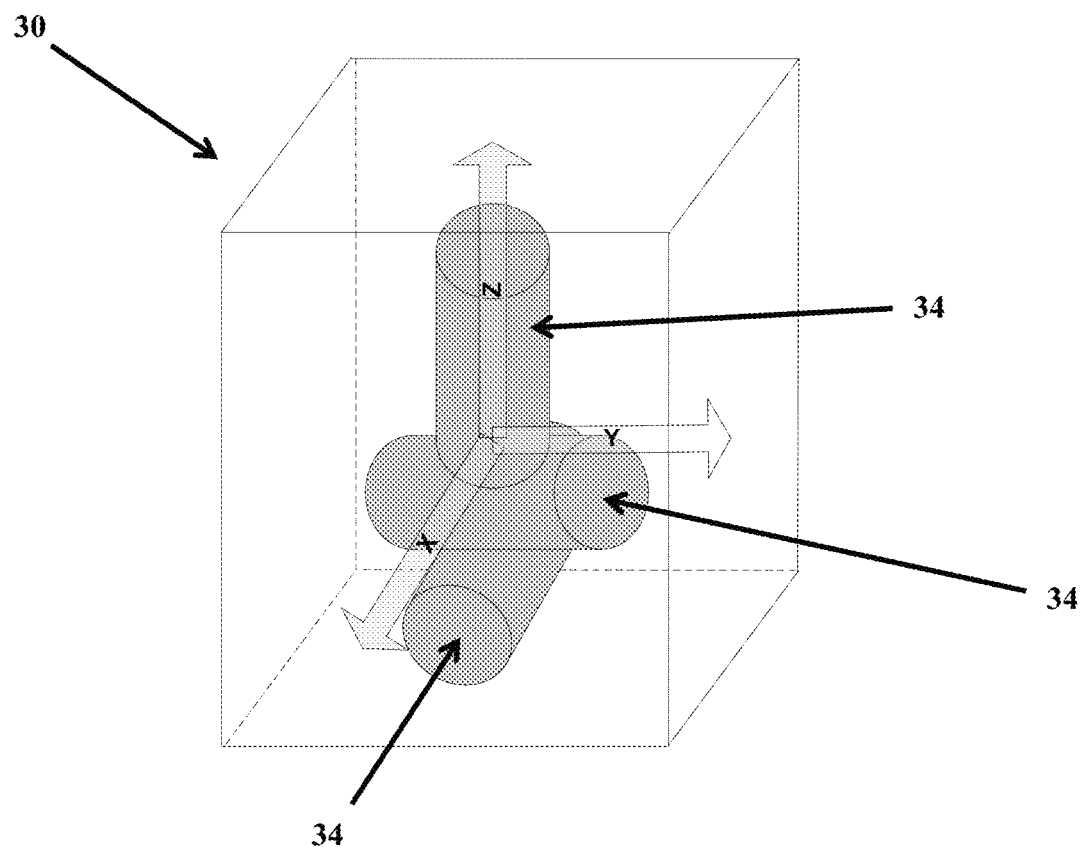
FIG. 3 shows an exemplary witness station (30) configuration having three orthogonal coils (35) arranged to minimize cross-talk.

In some embodiments, each witness station contains 1-3 witness antennas oriented orthogonally to each other and further arranged to have minimum cross-talk (i.e., interference with one another). FIG. 3 shows an exemplary configuration of a witness station 30, with three detection coils 34 (aka antennas), one oriented in the x plane, one in the y plane, and one in the z plane.

Figure 2:
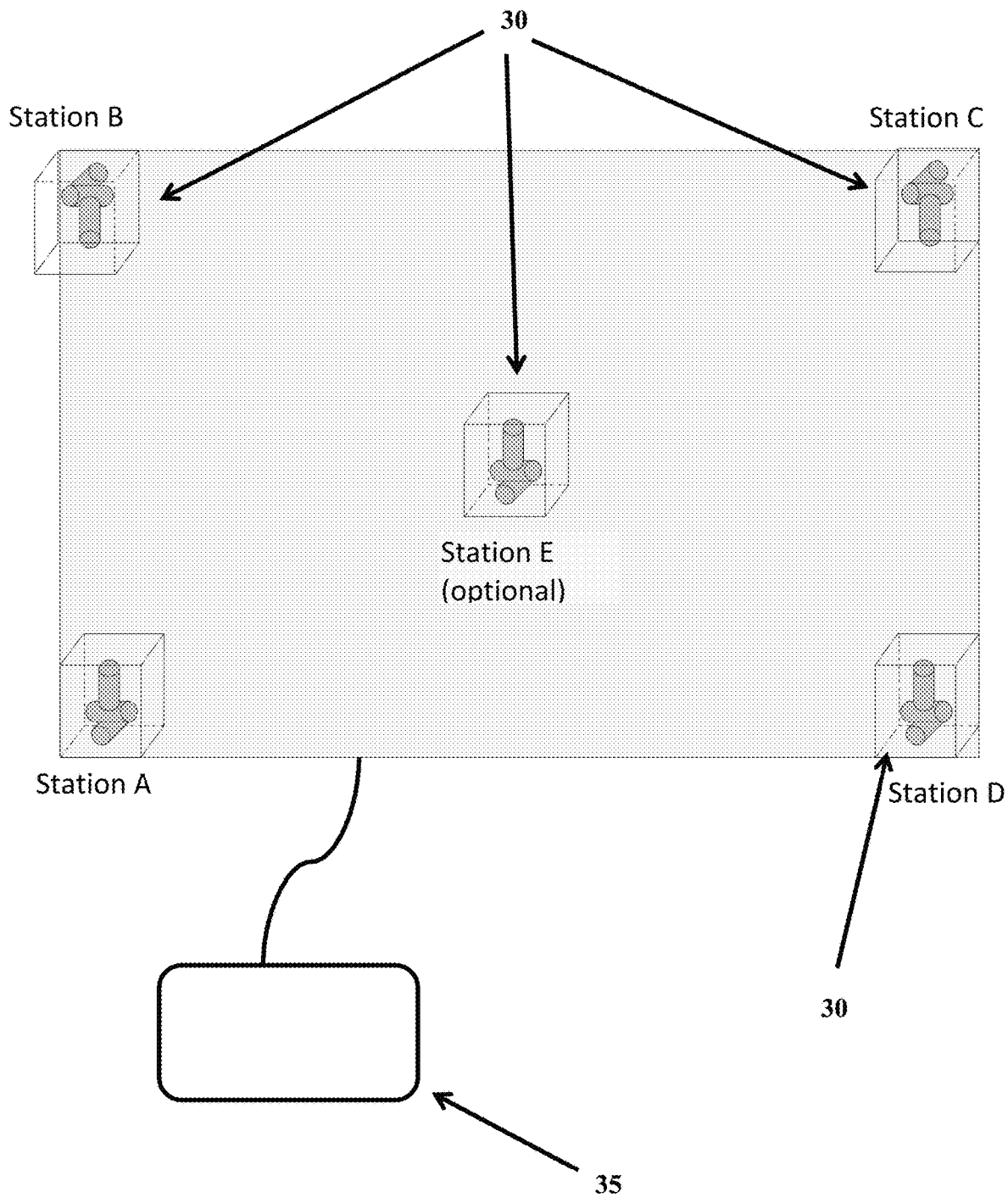
FIG. 2 shows an exemplary pad configuration with multiple witness stations (30).

FIG. 2 shows an exemplary arrangement of witness stations 30 within a flat pad with four witness stations 30 positioned at each of the four corners (labeled Station A, Station B, Station C, and Station D) and a fifth optional station (Station E) positioned in the center. Any number of stations may be employed (e.g., 1, 2, 3, 4, 5, 6, 7, 8, 9, 10, 11, 12, etc.) in any desired position and orientation. FIG. 2 further shows an electronics component 35 that is configured for receiving and processing the signals received by the witness station.

FIG. 1 shows an exemplary configuration of a witness station configuration as shown in FIG. 2 in three-dimensional space relative to three tags 100 located in an object above the witness station and relative to an attachment component 10 (e.g., a wand attached to a surgical instrument) having two locator emitters 70. FIG. 1 is shown with five witness stations 30.

The component housing the witness stations further comprises one or more receiver channels for collecting information obtained by the antennas of the witness stations. In some embodiments, the receiver comprises or consists of one or more channels, each channel fed by one or more (via a multiplexing switch) witness antennas.

In some embodiments, location of an implanted tag or an emitter on a medical device is accomplished geometrically by measuring the quasi-simultaneous power detected from these tags at multiple (e.g., four or more) witness stations, and using the power differences to perform vector math that determines the location of the tag without ambiguity. In some embodiments, this process is facilitated by a preliminary calibration using a known tag in a known location prior to the procedure.

In some embodiments, vectors describing the location of implanted tags or medical device emitters are used to provide visualization guidance to the surgeon about the spatial relationship of the medical device (particularly its tip) to the implanted tag, or (with computational guidance) to a lesion boundary. Multiple emitters on the medical device further provide vectors to determine the medical device's principal axis using the same vector math.

In some embodiments, the component comprising the witness stations comprises an analog front-end. For example, the analog input to the receiver may comprise or consists of a current-to-voltage (transimpedance instrumentation) preamplifier (see "www." Followed by "analog.com/en/products/amplifiers/instrumentation-amplifiers/ad8421.html#product-overview") whose output drives a synchronous detector (see "www." followed by "analog.com/en/products/rf-microwave/iq-modulators-demodulators/iq-demodulators/ad630.html#product-overview") that takes the unknown signal from the witness antennas and compares it to the known CW exciter signal, effectively filtering out the strong exciter signal and providing the amplitude modulation frequency of the tag as its output. This function is similar to that of a lock-in amplifier, where the (unmodulated) frequency reference is used to place a narrow-band notch filter onto the reference, recovering a much smaller modulation in the presence of noise.

In some embodiments, subsequent stages in the analog front-end provide additional bandpass and low-pass filtering and gain. For example, in some embodiments, the output of these stages is provided to a precision rectifier to directly determine a DC voltage proportional to the received signal strength from the instant antenna, or the unrectified signal is digitized using conventional D/A techniques.

In some embodiments, a digital back-end of the receiver accepts as input either a digital version of the DC voltage level or first performs a digital demodulation of the AC signal. Either approach results in a numerical indication of the signal strength due to the instant antenna. This signal varies with distance d between the instant witness antenna and the tag according to an inverse integer power relationship, e.g. $1/d^6$. Detailed considerations of the variation of signal strength with distance are found in "http://" followed by "robotics.eecs.berkeley.edu/~pister/290Q/Papers/Antennas%20propagation%20interference/near%20field%20path%20loss.pdf."

Consulting the above reference and inverting the experimentally-determined near-field signal strength versus distance relationship (e.g. $1/d^6$) enables the magnitude of a given distance vector to be determined with accuracy. Accumulating signal strengths and corresponding (post-calibration) distances from all active channels, an acceptably self-consistent solution to tag location in a given grid relative to the witness antennas is determined. One witness antenna can be designated as the origin of a world coordinate system, and all subsequent distances determined from that point. This can be done for both implanted tag signals and signals from the emitters associated with a surgical tool.

In some embodiments, location data for the tag as well as for the emitters is used to provide indications to the surgeon of tag-medical device distance. In some embodiments, this information is presented in relative format, e.g. one or more visual indicators of tag direction relative to the tip of the medical device. It can also be more quantitative, e.g. a number of bars or lights corresponding to the number of centimeters between the tag and the medical device tip. In some embodiments, further use of the distance data is employed for rendering a simple image of the medical device and its relative orientation and distance to the tag.

The emitters associated with a medical device may comprise any feature that creates a detectable signal in a magnetic field. In some embodiments, the emitter is of the nature of any of the tags described herein. In some embodiments, coils mounted onto a surgical tool or otherwise used for calibration may be driven directly with a modulated version of the exciter signal from the activation device so that these coils serve as substitute tags and can be located by the receiver of the witness stations component in the same manner as an implanted tag. The modulation to drive these coils can be accomplished with a conventional switch or frequency mixer as modulator, or by numerical means via a digital synthesizer.

The component that contains the emitters may further comprise a display to assist the user in directing the medical device to the tag during a surgical procedure. In some such embodiments, a visual or audio display is provided on or associated with the medical device that receives location information about the tag from the computer system. The display may be one or more directional indicators such as LEDs, that indicate direction and/or distance to the tag. Color changes may be employed to indicate "on target" versus "off target" positions. In certain embodiments, the display comprises a first display for presenting distance to tag information (e.g., visual, audible, lights, color, vibration, tactile, etc.); a second display for presenting vertical axis orientation, such as a preset preferred angle for approaching a tag in a patient (e.g., a visual, audible, lights, colors, vibration, tactile, etc. display); and/or a third display for presenting horizontal orientation (e.g., left to right information so the surgical device can be centered when approaching the tag). In some embodiments, the display comprises a plurality of displays (e.g., visual, audible, sensory, etc.) that allow the correct pitch and yaw axes to be employed (to minimize non-target tissue damage), and/or further a display that provides distance to tag information. In certain embodiments, a series of lights and/or sounds are provided on the display that guide the surgeon (e.g., the surgeon attempts to keep the lights in a center of an "X" series of lights, and/or to keep the volume of warning sounds off or as low as possible).

The technology is not limited by the mode of tag placement and a wide variety of placements techniques are contemplated including, but not limited to, open surgery, laparoscopy, endoscopy, via endovascular catheter, etc. The tags may be placed by any suitable device, including, but not limited to, syringes, endoscopes, bronchoscopes, extended bronchoscopes, laparoscopes, thoracoscopes, etc. An exemplary protocol is provided below.

A patient previously identified as having a breast tumor is admitted to a medical facility. The patient is initially sent to radiology. The radiologist examines prior imaging information identifying the target tumor. The subject is administered a local anesthetic, usually lidocaine or a derivative, using a needle introduced percutaneously. The subject is positioned in an imaging device, generally either ultrasound, conventional mammography, or a stereotactic unit. The location of the tumor is determined. An introducer needle (usually 6-20 gauge) is inserted either into or just proximal to the tumor and a biopsy needle is placed through the introducer needle and a specimen is obtained using a variety of methods (suction, mechanical cutting, freezing to fix the position of the tissue followed by mechanical cutting). After the specimen is obtained and sent for pathologic examination, a 6-20 gauge tag delivery needle is inserted into the coaxial introducer needle to the tissue with the distal open end positioned at the lesion. A tag is inserted into the proximal end of the delivery needle and delivered by plunger through the opening at the distal end of the needle and into the tissue. Likewise, the tag could have been pre-positioned at the distal end of the delivery needle. Proper location of the tag is confirmed via imaging. The delivery needle is withdrawn, leaving the tag in place in the breast tissue.

This type of procedure can be performed in an analogous manner in virtually any body space, organ, or pathologic tissue with the intent of localizing that tissue or space for further diagnosis or treatment of any kind. Areas of particular interest include but are not limited to the following organs, and disease processes that take place within them: brain, skull, head and neck, thoracic cavity, lungs, heart, blood vessels, gastrointestinal structures, liver, spleen, pancreas, kidneys, retroperitoneum, lymph nodes, pelvis, bladder, genitourinary system, uterus, ovaries, and nerves.

In some embodiments, during surgery, the patient is placed onto an operating table with the surgical area exposed and sterilized. The surgeon is provided with the imaging information showing the location of the target tissue (e.g., tumor) and tag. An incision is made at the location of the entry point of the placement needle. The remote activating device is placed in proximity to the tissue to activate the tag. The detection component comprising the witness stations detects a signal from the tag and allows the surgeon to guide the direction medical device toward the tumor. Once the tumor is localized, the surgeon removes the appropriate tissue and, optionally, removes the tag.

In some embodiments, the system finds use in surgery with the tags placed as fiducials on or in the body. The relative position of the tags and any surgical instruments is located using the electromagnetic field. This information is communicated to a physician in real-time using a variety of methods including by not limited to visual (computer screens, direction and depth indicators using a variety of methods, haptic feedback, audio feedback, holograms, etc), and the position of the instruments displayed on any medical images such as CT, MRI, or PET scans in 2D or 3D. This data finds use to guide the physician during a procedure, or is used as a training method so that physicians can perform a virtual procedure. Such system may be integrated into or provide alternative approaches to existing surgical systems, such as the STEALTH system (Medtronic) for applications such as neurosurgeries.

Figure 6:
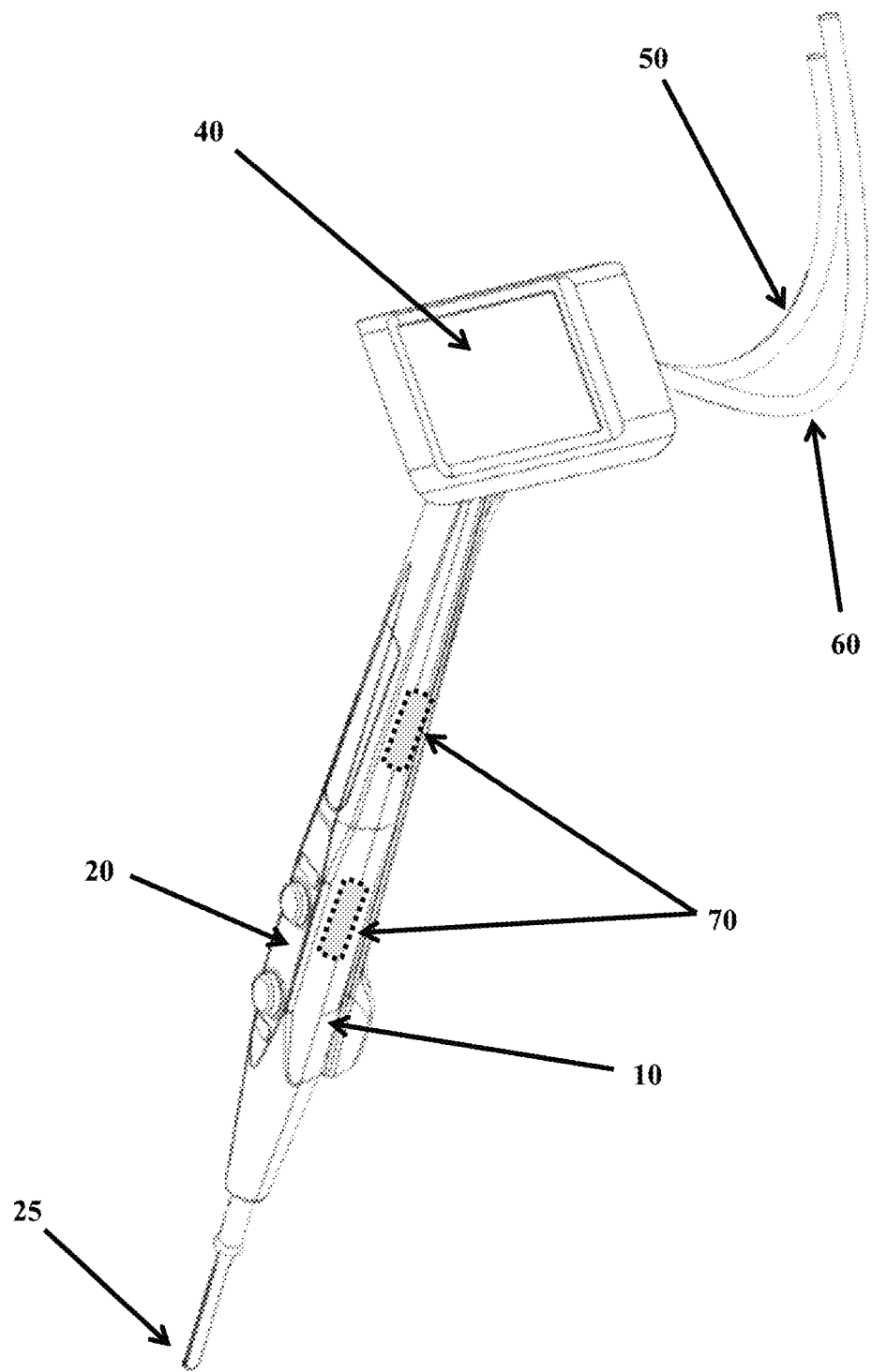
FIG. 6 shows an attachment component 10 that is attached to a medical device 20, which has a device tip 25. The attachment component 20 has two location emitters 70 located therein. The attachment component 10 is attached to, or integral, with a display component 40.

FIG. 6 shows an attachment component 10 that is attached to a medical device 20, which has a device tip 25. The attachment component 20 has two location emitters 70 located therein. In certain embodiments, the attachment component has one, two, three, four, five or more location emitters. The attachment component 10 is attached to, or integral, with a display component 40. In particular embodiments, the display component 40 is adjustable (e.g., for preferred angle of viewing), and is configured to be in the line of site of a surgeon performing a procedure using the medical device 20. The medical device (e.g. a BOVIE surgical instrument) is attached to a medical device wire 50 (e.g.., to provide power, and/or to provide instructions to turn the device off when a remote activating device is turned on). The attachment component 10 is attached to an attachment component wire 60 (e.g., to provide power and/or provide signal information from the emitters 70 to a an electronics component that receives and processes signals from witness stations). In certain embodiments, the attachment component is wirelessly connected to the electronics component (e.g., no wire 60), and has internal battery power.

Figure 7:
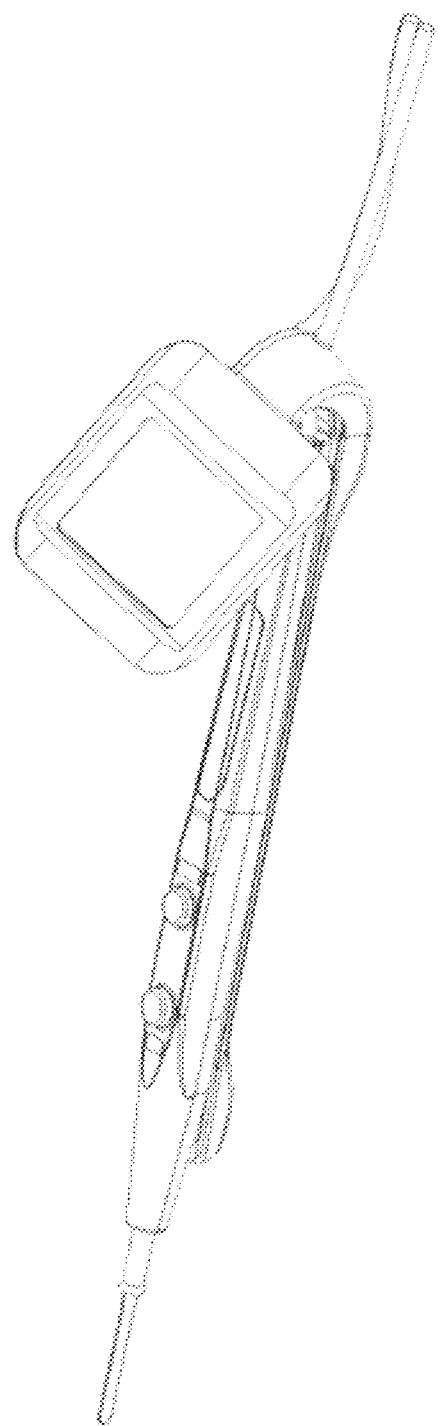
FIG. 7 shows an attachment component that is attached to a medical device. The attachment component is attached to a display component, which is angled generally toward the tip of the medical device.

FIG. 7 shows an attachment component that is attached to a medical device. The attachment component is attached to a display component, which can be moved into different positions based on the user's preference. FIG. 7 shows the display component angled generally toward the tip of the medical device.

Figure 8:
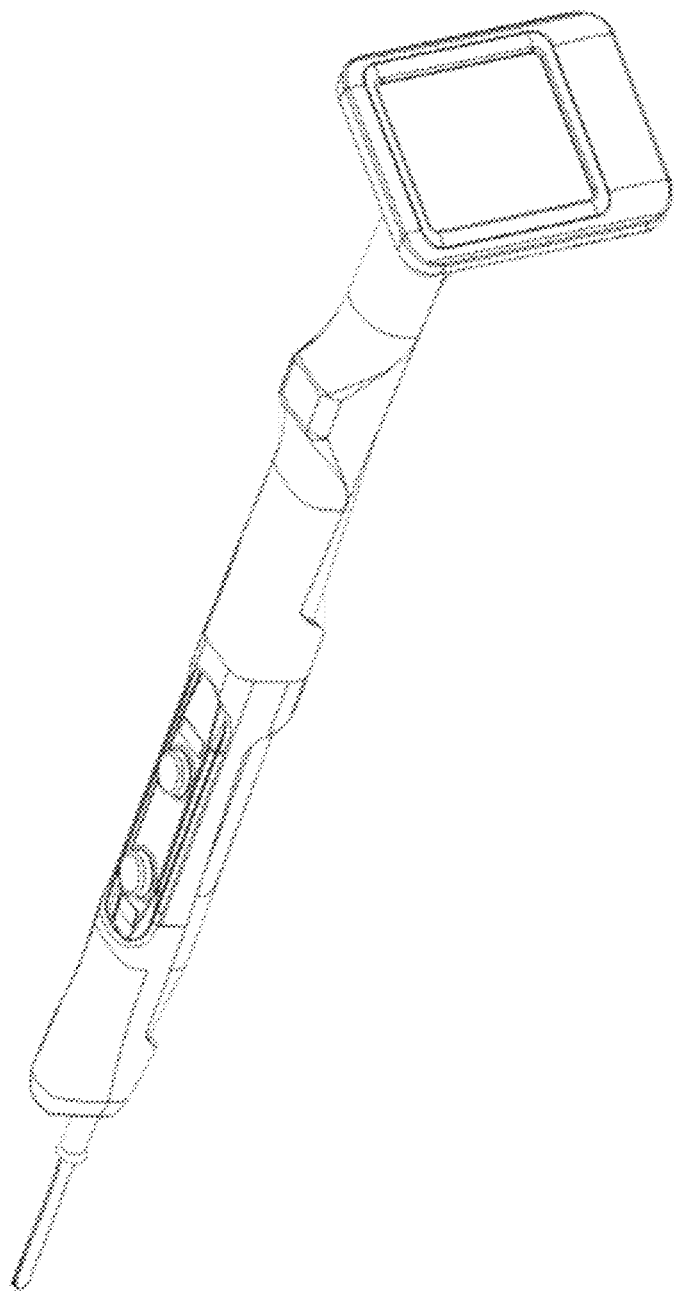
FIG. 8 shows an attachment component that is attached to a medical device. The attachment component is attached to a display component, which is angled generally perpendicular with regard to the tip of the medical device.

FIG. 8 shows an attachment component that is attached to a medical device. The attachment component is attached to a display component, which can be moved into different positions based on the user's preference. FIG. 8 shows the display component angled generally perpendicular with regard to the tip of the medical device.

Figure 9:
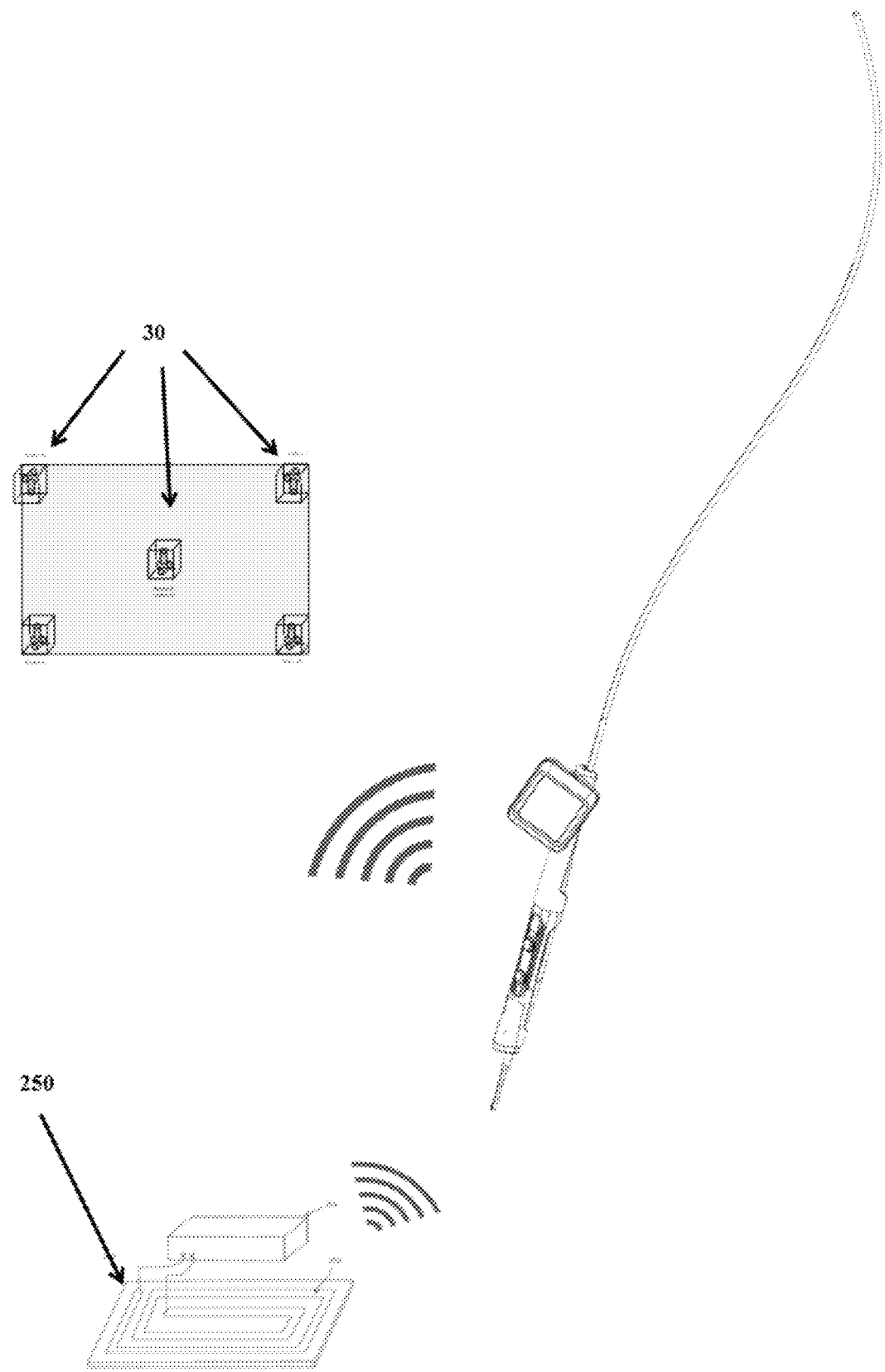
FIG. 9 shows an attachment component that is attached to a medical device. The attachment component, having one, two, three or more location emitters therein or thereon, is shown receiving a signal from a remote activating device 250. The location emitters then provide a signal (e.g., sideband signal) to the witness stations 30, which may be separate (as depicted in FIG. 9) or integrated into the remote activating device.

FIG. 9 shows an attachment component that is attached to a medical device. The attachment component, having one, two, three or more location emitters therein or thereon, is shown receiving a signal from a remote activating device 250. The location emitters then provide a signal (e.g., sideband signal) to the witness stations 30, which may be separate (as depicted in FIG. 9) or integrated into the remote activating device.

FIGS. 10-14 show embodiments of the present disclosure where the movements of a medical device 20, with a device tip 25, are tracked via location emitters in an attachment component 10 (attached to the medical device 20), and displayed in real time on the display component in relation to the tag 100 (e.g., which could be in a tissue of a patient, or, outside a patient on a table top to ensure proper functioning before any surgery).

FIG. 10A (side view) and FIG. 10B (top view) show an attachment component 10 attached to a medical device 20, having a distal tip 25, where a human hand is holding the medical device+attachment component combination. The attachment component 10 has one, two, three or more location emitters 70 therein (not pictured; see FIG. 6), which allows the three-dimensional orientation of the medical device 20 and device tip 25 to be determined relative to the tag 100 and displayed on display component 40. FIG. 10C shows a display component 40 that includes a display screen 45. The display screen may be any type of screen able to depict images, such as, for example, a cathode ray tube display (CRT), light-emitting diode display (LED), electroluminescent display (ELD), electronic paper (E Ink), plasma display panel (PDP), liquid crystal display (LCD), organic light-emitting diode display (OLED), etc. In particular embodiments, the display screen is see-through, providing a heads up display that allow a user to view images on the screen, but still being able to look through the screen (e.g., to see the surgical field to enable augmented or virtual reality capabilities). In certain embodiments, the display screen 45 has an area of about 2-9 inches squared (e.g., 2 . . . 4 . . . 6 . . . 8 . . . or 9 inches squared). The display screen shown in FIG. 10C displays: 1) a total distance indicator 80 (e.g., the distance of the device tip 25 to the tag 100 taking into account X, Y, and Z dimensions); 2) a tag indicator (e.g., schematic image) 101 that corresponds to the location of the actual tag 100; 3) a medical device indicator (e.g., schematic image) 21 and device tip indicator (e.g., schematic image) 26, which correspond to the actual medical device 20 and device tip 25, where said medical device indicator (e.g., schematic image) 21 and device tip indicator (e.g., schematic image) 26 move in real time on the display screen 45 to track the location (e.g., in X and Y dimensions) of the actual medical device 20 and device tip 25 relative to the tag 100; 4) a tag-tip vector indicator (e.g., schematic image) 85, which extends from the tag indicator (e.g., schematic image) 101 to the device tip indicator (e.g., schematic image) 26, providing the visual representation of the two-dimensional (X and Y) location of the device tip 25 with respect to the tag 100, as well as a visual representation of the two-dimensional (X and Y) distance of the device tip 25 to the tag 100; and 5) a depth indicator 90, which provides a visual indicator of how high above or below the device tip 25 is compared to the tag 100 (e.g., provides Z value for the device tip 25 compared to the tag 100). The depth indicator 90 may be presented, for example, as a number or, as shown in FIG. 10C, a magnitude indicator (e.g., where the magnitude is greater the closer the device tip 25 gets to the tag 100). In certain embodiments, the depth indicator 90 also shows X and/or Y offset with respect to the tag 100 (e.g., FIG. 10C shows X offset).

Figure 10:
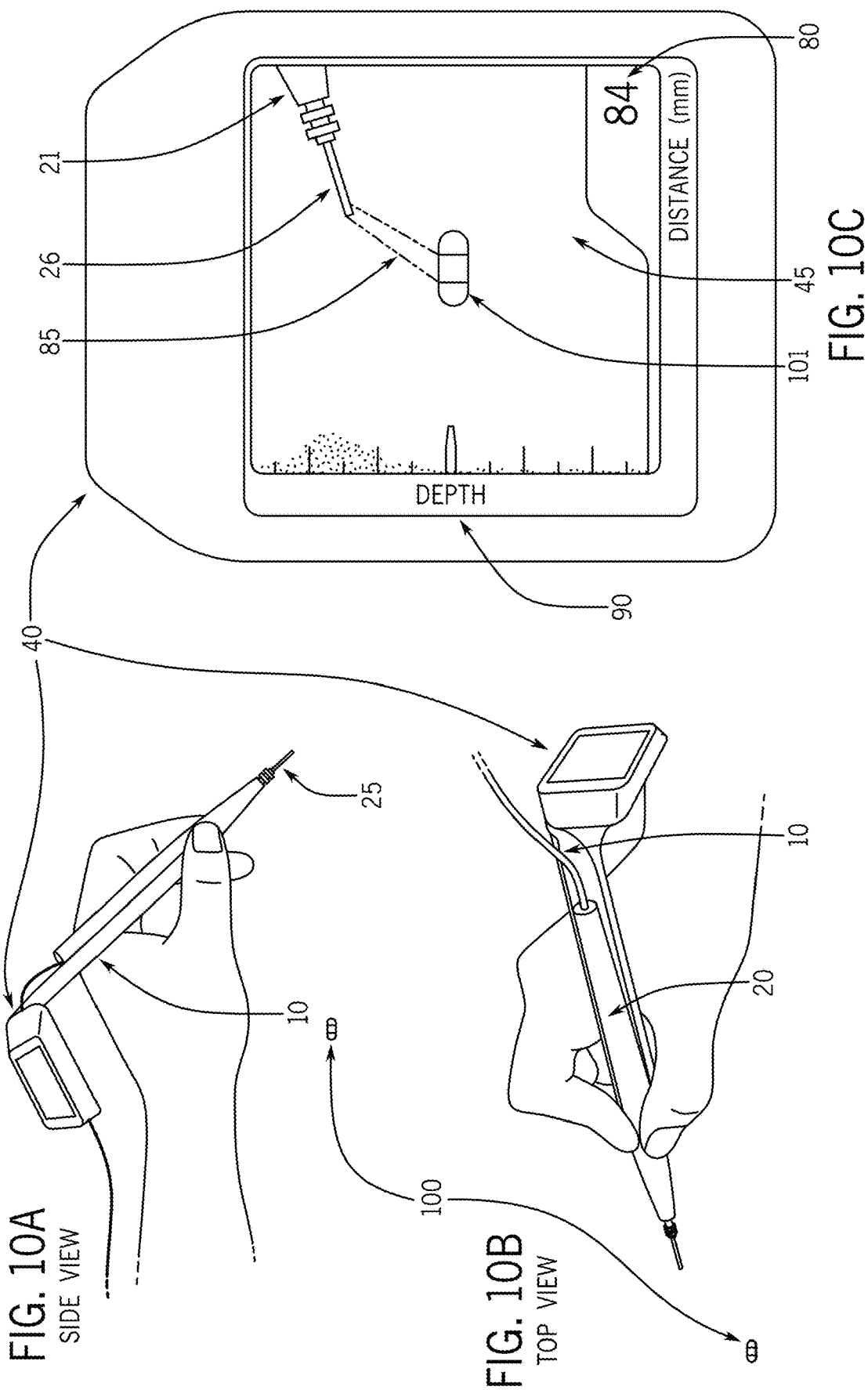
FIGS. 10A-10C.

FIG. 11 shows the same components as FIG. 10, showing how all of the following move or change on the display screen 45 when the medical device 25 with attached attachment component 10 are moved by a human hand to a different position than in FIG. 10: the tag indicator (e.g., schematic image) 101, tag-tip vector indicator (e.g., image) 85, device tip indicator (e.g., image) 26, medical device indicator (e.g., schematic image) 21, total distance indicator 80, and depth indicator 90.

FIG. 12 shows the same components as FIGS. 10 and 11, and shows how all of the following move or change on the display screen 45 when the device tip 25 is hovered 29 mm directly over the tag 100: the tag indicator (e.g., schematic image) 101, tag-tip vector indicator (e.g., schematic image) 85, device tip indicator (e.g., schematic image) 26, medical device indicator (e.g., schematic image) 21, total distance indicator 80, and depth indicator 90.

FIG. 13 shows the same components as FIGS. 10-12, and shows the device tip 25 at, or very close, to zero mm's above the tag, which is shown visually on the display screen 45 as a large peak on the depth indicator 90.

FIG. 14 shows the same components as FIGS. 10-13, but shows the total distance indicator 80 near the device tip image 26, rather than in the lower right hand corner of the display screen 45. FIG. 14 also shows a plurality of guide rings 95 centered on the tag indicator (e.g., schematic image) 101, which provide, for example, a set distance from the tag 100 (e.g., allowing a surgeon to use these as guides for cutting tissue).

FIG. 15 shows the same components as FIG. 14, where the device tip 25 has been moved to be centered over the tag 100, thereby causing the tag indicator 101 to light up brighter, providing a visual signal to a user that the device tip 25 is centered over the tag 100.

In some embodiments, information about the location of the tag or tags or the surgical paths or routes to the tags is conveyed to a surgeon or other user in a manner that comprises one or more augmented reality or virtual reality components. For example, in some embodiments, a surgeon wears or accesses a virtual reality device (e.g., goggles, glasses, helmet, etc.) that shows a partial or complete virtual image of the patient or surgical landscape. Tag position information collected and calculated by the systems described herein are represented by one or more visual components to the surgeons to assist in accurate targeting of the tag or tags. For example, the tissue containing the tag may be represented with a virtual image of the tag location shown. Likewise, in some embodiments, a surgical pathway is visually presented, for example, as a colored line to be followed. In some embodiments employing augmented reality features, a display, such as those shown in FIGS. 6-15, presents a graphical or video capture of the patient representative of what the surgeon would visualize if the monitor were not present and overlays one or more augmented features on the display. The graphical or video display data may be captured by one or more cameras in the surgical field. The augmented features include, but are not limited to, a representation of the location of the tag in the target tissue, a projected surgical path, a target point to which the surgeon aligns the tip of the surgical device, a simulated surgical margin zone to treat, arrows or other location indicators that recommend movement if the optimal pathway is deviated from, or the like. In some embodiments, this augmented reality view provides an alternative view setting to those shown in FIGS. 10-15. In some embodiments, the surgeon toggles between the view settings by pushing a button or by other mechanism (e.g., voice command). In some embodiments, a view setting allows both features to be observed together.

We claim:

1. A system comprising:
   a pad including an excitation coil and a plurality of witness stations;
   a medical device;
   a first location emitter attached to the medical device; the first location emitter configured to generate a first signal in response to a magnetic field generated by the excitation coil;
   a second location emitter attached to the medical device; the second location emitter configured to generate a second signal in response to the magnetic field generated by the excitation coil;
   a tag physically separate from and not physically linked to the medical device; the tag configured to generate a third signal in response to the magnetic field generated by the excitation coil; and
   a processor that determines a location of the medical device based on the first signal and the second signal detected by the plurality of witness stations, and a location of the tag based on the third signal detected by the plurality of witness stations.

2. The system of claim 1, further comprising:
   a display component including a display screen;
   wherein the display screen is configured to display the location of the medical device relative to the location of the tag.

3. The system of claim 2, wherein the display screen displays a tag indicator that corresponds to the location of the tag.

4. The system of claim 3, wherein the display screen further displays a plurality of guide rings centered on the tag indicator.

5. The system of claim 2, wherein the display screen displays a total distance indicator which indicates the distance between the medical device and the tag.

6. The system of claim 2, wherein the display screen displays a medical device indicator that corresponds to the location of the medical device.

7. The system of claim 6, wherein the display screen further displays a directional indicator the provides information for moving or positioning the medical device.

8. The system of claim 7, wherein the directional indicator comprises an image of the medical device that is distinct from the medical device indicator.

9. The system of claim 2, wherein the display screen displays a tag-tip vector indicator that provides a representation of the two-dimensional distance, and two-dimensional location, of a device tip of the medical device to the tag.

10. The system of claim 2, wherein the display screen displays a depth indicator that provides an indication of how high above, or below, the hand-held medical device is with respect to the tag.

11. The system of claim 2, wherein the display screen is at least partially see through, which allows a user to view images on the display screen while still being able to look through the display screen.

12. The system of claim 2, wherein the display screen further displays one or more guides for performing a procedure.

13. The system of claim 12, wherein the one or more guides comprises symbols directing a user how to move the medical device to accomplish a task.

14. The system of claim 2, further comprising an attachment component that is configured to attach to the medical device, wherein the first location emitter and the second location emitter are located within the attachment component; and wherein the display is attached to or integral with the attachment component.

15. The system of claim 1, wherein the tag emits a sideband at a frequency defined by a number programmed into the tag.

16. The system of claim 1, wherein the tag includes a coil antenna.

17. The system of claim 16, wherein the coil antenna is coupled to an integrated circuit, and the coil antenna resonates at 100-200 kHz.

18. The system of claim 1, wherein the pad is configured to be placed in proximity to a patient having the tag embedded in the patient.

19. The system of claim 1, wherein the plurality of witness stations includes a lock-in amplifier tuned to a frequency of a sideband from the tag.

20. The system of claim 1, wherein the processor determines an orientation of the medical device based on the first signal and the second signal detected by the plurality of witness stations.

21. The system of claim 1, further comprising an attachment component that is configured to attach to the medical device, wherein the first location emitter and the second location emitter are located within the attachment component.

22. The system of claim 21, wherein the attachment component comprises a sheath that slides over the medical device or a clip that clips onto the medical device.

23. The system of claim 1, wherein the first location emitter and the second location emitter are integrated into the medical device.

24. The system of claim 1, wherein the medical device is a robotic surgical system.

* * * * *